US008138324B2

(12) United States Patent
De Gier et al.

(10) Patent No.: US 8,138,324 B2
(45) Date of Patent: Mar. 20, 2012

(54) EXPRESSION SYSTEM FOR PROTEINS

(75) Inventors: Jan Willem De Gier, Stockholm (SE); Samuel Wagner, New Haven, CT (US)

(73) Assignee: Xbrane Bioscience AB, Stockholm (SE)

(*) Notice: Subject to any disclaimer, the term of this patent is extended or adjusted under 35 U.S.C. 154(b) by 354 days.

(21) Appl. No.: 12/395,102

(22) Filed: Feb. 27, 2009

(65) Prior Publication Data
US 2009/0280536 A1 Nov. 12, 2009

(30) Foreign Application Priority Data
Feb. 29, 2008 (SE) ........................................ 0800483

(51) Int. Cl.
C07H 21/04 (2006.01)
C07H 21/02 (2006.01)
C12P 1/00 (2006.01)

(52) U.S. Cl. ...................... 536/23.7; 536/23.1; 536/23.2; 435/41; 435/69.1; 435/69.2; 435/71.1; 435/440; 435/471

(58) Field of Classification Search .................. 536/23.1, 536/23.2, 23.7; 435/41, 69.1, 69.2, 71.1, 435/440, 471
See application file for complete search history.

(56) References Cited

U.S. PATENT DOCUMENTS
5,679,533 A 10/1997 Szafranski et al.
5,830,694 A 11/1998 Studier et al.
2007/0122881 A1 5/2007 Surber FOREIGN PATENT DOCUMENTS
EP 1 847 611 A2 10/2007
WO WO 2006/061174 A2 6/2006
WO WO 2008/017073 A2 2/2008

OTHER PUBLICATIONS

Amann et al., "ATG vectors for regulated high-level expression of cloned genes in *Escherichia coli*," Gene, vol. 40, 1985, pp. 183-190.
Brosius, "Toxicity of an overproduced foreign gene product in *Escherichia coli* and its use in plasmid vectors for the selection of transcription terminators," Gene, vol. 27, 1984, pp. 161-172.
Dower et al., "T7 RNA polymerase-directed transcripts are processed in yeast and link 3' end formation to mRNA nuclear export," RNA Journal, vol. 8, 2002, pp. 686-697.
Dubendorff et al., "Controlling Basal Expression in an Inducible T7 Expression System by Blocking the Target T7 promoter with *lac* Repressor," J. Mol. Biol., vol. 219, 1991, pp. 45-59.
Giacalone et al., "Toxic protein expression in *Escherichia coli* using a rhamnose-based tightly regulated and tunable promoter system," BioTechniques, vol. 40, No. 3, 2006, pp. 355-363.
Goeddel et al., "Human leukocyte interferon produced by *E. coli* is biologically active," Nature, vol. 287, Oct. 2, 1980, pp. 411-416.
Holcroft et al., "Interdependence of Activation at *rhaSR* by Cyclic AMP Receptor Protein, the RNA Polymerase Alpha Subunit C-Terminal Domain, and RhaR," Journal of Bacteriology, vol. 182, No. 23, Dec. 2000, pp. 6774-6782.

Jeruzalmi et al., "Structure of T7 RNA polymerase complexed to the transcriptional inhibitor T7 lysozyme," The EMBO Journal, vol. 17, No. 14, 1998, pp. 4101-4113.
Kang et al., "One step engineering of T7-expression strains for protein production: Increasing the host-range of the T7-expression system," Protein Expression and Purification, vol. 55, 2007, pp. 325-333.
Miroux et al., "Over-production of Proteins in *Escherichia coli*: Mutant Hosts that Allow Synthesis of some Membrane Proteins and Globular Proteins at High Levels," J. Mol. Biol., vol. 260, 1996, pp. 289-298.
Nguyen et al., "Bacteriophage T7 RNA polymerase-directed, inducible and tissue-specific over-expression of foreign genes in transgenic plants," Plant Biotechnology Journal, vol. 2, 2004, pp. 301-310.
Polkinghorne et al., "Transient expression in insect cells using a recombinant baculovirus synthesizing bacteriophage T7 RNA polymerase," Nucleic Acids Research, vol. 23, No. 1, 1995, pp. 188-191.
Skerra, "Use of the tetracycline promoter for the tightly regulated production of a murine antibody fragment in *Escherichia coli*," Gene, vol. 151, 1994, pp. 131-135.
Wagner et al., "Rationalizing membrane protein overexpression," TRENDS in Biotechnology, 2006, pp. 1-8.
Wang et al., "Facilitated in vivo synthesis of ribonucleic acid and protein via T7 RNA polymerase," Analytical Biochemistry, vol. 375, 2008, pp. 97-104.
Yanisch-Perron et al., "Improved M13 phage cloning vectors and host strains: nucleotide sequences of the M13mp18 and pUC19 vectors," Gene, vol. 33, 1985, pp. 103-119.
McKinney et al., Tightly Regulated Gene Expression system in *Salmonella enterica* Serovar Typhimurium, (2002), Journal of Bacteriology, vol. 184, No. 21, pp. 6056-6059.
Hartnett et al., "The Single Step (KRX) Component Cells: Efficient Cloning and High Protein Yields," (Aug. 2006), Promega Notes, No. 94, pp. 27-30.
Studier et al., "Use of Bacteriophage T7 Lysozyme to Improve and Inducible T7 Expression System," (1991), Journal of Molecular Biology, vol. 219, pp. 37-44.
Spehr et al., "Improvement of the T7 expression by the use of T7 lysozyme," (2000), Gene vol. 257, pp. 259-267.
Moffatt et al., "T7 Lysozyme Inhibits Transcription by T7 RNA Polymerase,"(1987), Cell, vol. 49, pp. 221-227.
Giaclone et al., "Toxic protein expression in *Escherichia coli* using a rhamnose-based tightly regulated and tunable promoter system," (2006), BioTechniques vol. 40, No. 3, pp. 355-363.

(Continued)

Primary Examiner — Rodney P. Swartz
(74) Attorney, Agent, or Firm — Drinker Biddle & Reath LLP

(57) ABSTRACT

The invention provides a novel system for the tunable expression of nucleic acids encoding e.g., polypeptides such as recombinant proteins in prokaryotic systems. The system is based on the ability of T7 lysozyme (T7Lys) to inhibit the activity of T7RNAP. Expression of T7Lys can be continuously adjusted as its expression is under the control of a promoter whose activity can be titrated. The invention provides a host cell capable of expressing T7 RNA polymerase, the host cell comprising a first nucleic acid having a T7 lysozyme gene or a T7 lysozyme variant gene and a tunable promoter for controlling the expression of the T7 lysozyme gene. It also provides a host cell further comprising a second nucleic acid having a T7 promoter operably linked to a nucleic acid sequence encoding a target polypeptide, whereby expression of the target polypeptide is tuned via controlling the expression of the T7 lysozyme gene.

20 Claims, 18 Drawing Sheets

OTHER PUBLICATIONS

Paul et al., "An artificial regulatory circuit for stable expression of DNA-binding proteins in a T7 expression system," (1997), *Gene* vol. 190, pp. 11-15.

Tolia et al., "Strategies for protein coexpression in *Escherichia coli*," (2006), *Nature Methods*, vol. 3, No. 1, pp. 55-64.

Studier et al., "Use of T7 RNA Polymerase to Direct Expression of Cloned Genes," in *Methods in Enzymol.*, vol. 185, pp. 60-89 (1990).

Drew et al., A scalable, GFP-based pipeline for membrane protein overexpression screening and purification, (2005), *Protein Science*, vol. 14, pp. 2011-2017.

Cheng et al., "The structure of bacteriophage T7 lysozyme, a zinc amidase and an inhibitor of T7 RNA polymerase," (1994), *Proc. Natl. Acad. Sci. USA*, vol. 91, pp. 4034-4038.

Wagner et al., "Tuning *Escherichia coli* for membrane protein overexpression," (2008), *PNAS*, vol. 105, No. 38, pp. 14371-14376, and Supporting Information by Wagner et al., 10.1073/pnas. 0804090105 available at www.pnas.org/cgi/contents/short/0804090105.

Wagner et al., "Consequences of Membrane Protein Overexpression in *Escherichia coli*," (2007), *Mol. & Cell. Proteomics*, vol. 6, pp. 1527-1550.

Kessler et al., "Identification of a *cis*-acting Sequence within the *Pm* Promoter of the TOL Plasmid which confers XylS-mediated Responsiveness to Substituted Benzoates," (1993), *Journal of Molecular Biology*, vol. 230, pp. 699-703.

Wanarska et al., "A freeze-thaw method for disintegration of *Escherichia coli* cells producing T7 lysozyme used in pBAD expression systems," (2007), *Acta Biochimica Polonica*, vol. 54, No. 3, pp. 671-672.

Ikeda et al., "Inhibition of T7 RNA Polymerase by T7 Lysozyme in Vitro," (1992), *The Journal of Biological Chemistry*, vol. 267 No. 28, pp. 20153-20158.

Schweder et al., "*Escherichia coli* K12 *relA* strains as safe hosts for expression of recombinant DNA," (1995) *Applied Microbiology and Biotechnology*, vol. 42, pp. 718-723.

Yun et al., "Development of a Novel Vector System for Programmed Cell Lysis in *Escherichia coli*," (2007) *Journal of Microbiology and Biotechnology*, vol. 17, pp. 1162-1168.

Liang et al. "Effective photoregulation of gene expression by photoresponsive T7 promoter,"(2007), *Nucleic Acids Symposiums Series* No. 51, pp. 349-350.

Asanuma et al., "Photo-regulation of transcription by RNA polymerase with azobenzene-tethered promoter," (2002), *Nucleic Acids Research*, Supplement No. 2, pp. 75-76.

Asanuma et al., "Photoregulation of the Transcription Reaction of T7 RNA Polymerase by Tethering an Azobenzene to the Promoter," (2002), *Chembiochem*, vol. 3, No. 8, pp. 786-789.

Saïda et al., "Expression of Highly Toxic Genes in *E. coli*: Special Strategies and Genetic Tools," (2006) *Current Protein and Peptide Science*, vol. 7, pp. 47-56.

Wang et al., "Improvement of the Thermoregulated T7Expression System by Using the Heat-Sensitive *lacI*," (2004), *Biotechnol. Prog.*, vol. 20, No. 5, pp. 1352-1358.

Chao et al., "High production of heterologous proteins in *Escherichia coli* using the thermo-regulated T7 expression system," (2002), *Applied Microbiology and Biotechnology*, vol. 58, No. 4, pp. 446-453.

Chao et al., "Stringent Regulation and High-Level Expression of Heterologous Genes in *Escherichia coli* Using T7 System Controllable by the *araBAD* Promoter," (2002) *Biotechnology Progress*, vol. 18, No. 2, pp. 394-400.

Wycuff et al., "Generation of an AraC-*ara*BAD Promoter-Regulated T7 Expression System," (2000) *Analytical Biochemistry*, vol. 277, No. 1, pp. 67-73.

US 8,138,324 B2

EXPRESSION SYSTEM FOR PROTEINS

CROSS REFERENCE TO RELATED APPLICATIONS

This application claims benefit of Swedish Application 0800483-0.

REFERENCE TO A SEQUENCE LISTING

A Sequence Listing providing SEQ ID NOS: 1-17 is incorporated by reference herein.

FIELD OF THE INVENTION

The invention relates to an expression system for polypeptides. In particular, the invention relates to plasmids and host cells for polypeptide expression, which can adjust expression intensity thereby improving expression yields. More specifically, the present invention relates to new vectors expressible in a host comprising an adjustable promoter operably linked to a nucleic acid sequence encoding T7 lysozyme. Furthermore, the invention relates to the use of these vectors for the expression of nucleic acids encoding T7 lysozyme. The invention relates also to the use of T7 lysozyme to adjust activity of T7 RNA polymerase in a way to yield optimal expression of nucleic acids encoding e.g., polypeptides, in particular proteins with complex post-translational biogenesis, e.g., membrane proteins, secretory proteins, proteins that are post-translationally modified (e.g., glycosylated), and proteins that require assistance of chaperones for their folding.

BACKGROUND TO THE INVENTION

Many systems have been described for the expression of nucleic acids encoding e.g., polypeptides such as recombinant proteins in prokaryotic systems. The T7 RNA polymerase (T7RNAP, SEQ ID NO:17) based expression systems are the most widely used systems to produce recombinant proteins in *Escherichia coli* (Studier, et al. (1990) Methods Enzymol 185:60-89). It is of note that besides in *E. coli*, T7RNAP based expression has been used in a host of different pro- and eukaryotic organisms (e.g., Kang et al. (2007) Protein Expr Purif. 55(2):325-33; Dower and Robasch (2002) RNA 8:686-697; Nguyen et al. (2004) Plant Biotechnol. J. 2: 301-310; Polkinghorne and Roy (1995) Nucleic Acids Res. 23(1): 188-191; Wang et al. (2007) Analytical Biochemistry, in press (doi:10.1016/j.ab.2007.11.037)). T7RNAP recognizes a very specific promoter, i.e., a T7 promoter (Chamberlin et al., (1970) Nature 228, 227-231; Oakley and Coleman (1977) PNAS 74, 4266-4270; Rosa (1979) Cell 16, 815-825; Panayotatos and Wells (1979) Nuci. Acids Res. 13, 2227-2240; Dunn and Studier (1983) J. Mol. Biol. 166, 477-535/ 175, 111-112), and transcribes DNA with an eight times higher transcription rate than *E. coli* RNA polymerase (Iost, et al. (1992) J Bacteriol 174:619-22). This is of great advantage for the high yield production of recombinant protein in *E. coli*. The down-side of good efficiency is e.g., the large metabolic burden and folding stress imposed onto the host cell. While the production of proteins in the cytoplasm of *E. coli* is relatively straightforward, overexpression of membrane proteins in *E. coli* remains a challenging task (Wagner, et al. (2006) Trends Biotechnol 24:364-71). Although membrane proteins can often easily be expressed in inclusion bodies, their refolding into functional proteins is usually not successful. Overexpression of membrane proteins through accumulation in the cytoplasmic membrane system avoids this refolding problem, but is usually toxic, thereby severely reducing yields. This is primarily caused by the complex requirements of membrane protein biogenesis where, after translation initiation at the ribosome, membrane protein ribosome nascent chain complexes get targeted to the cytoplasmic membrane (Luirink, et al. (2005) Annu Rev Microbiol 59:329-55). Transmembrane domains (TMDs) of membrane proteins get trapped in the Sec translocon and subsequently partition into the lipid bilayer. Membrane protein overexpression easily saturates one or several steps of the biogenesis pathway which leads to undesirable aggregation and degradation of recombinant protein in the cytoplasm. Furthermore, blockage of the secretory pathway results in severe toxicity for the host cell (Wagner, et al. (2007) Mol Cell Proteomics 6:1527-50). Reduced viability of the host cell and misfolding of the overexpressed recombinant protein result in low yields of the desired product. The major problem in this case is that expression of polypeptides by T7RNAP is too strong. Most T7RNAP based expression systems have relied exclusively on a fixed activity of T7RNAP resulting in a fixed intensity of recombinant protein expression. The most widely used strains for this purpose are BL21(DE3) and its derivatives BL21(DE3)pLysS, BL21(DE3)pLysE, C41(DE3) and C43 (DE3) (Studier (1991) J Mol Biol 219:37-44) (Miroux (1996) J Mol Biol 260: 289-98). Hosts carrying the pLysS and pLysE plasmids express T7 lysozyme, pLysS at a set low level and pLysE at a set high level. All of these fixed systems leave no opportunity to adjust the intensity of expression to the individual requirements of different target proteins. Since it is unpredictable what expression intensity is optimal for getting the best overexpression yields of a particular protein, expression has to be screened in different strains with fixed T7RNAP based expression intensities. It would be ideal if different expression intensities could be screened for in only one T7RNAP based expression system. Such "all in one" expression system would facilitate overexpression screening tremendously. Thus, there is a need to provide alternative prokaryotic and eukaryotic expression systems with the ability to continuously adjust the expression intensity of nucleic acid sequences, particularly those encoding membrane proteins and other polypeptides with complex post-translational biogenetic requirements; e.g., secretory proteins, proteins that are post-translationally modified (e.g., glycosylated (Wacker et al., (2002) Science 298, 1790 -1793), and proteins that require assistance of chaperones for their folding.

Finding the optimal T7RNAP based strain for the overexpression of a protein is a matter of time consuming 'trial and error', whereby e.g., BL21 (DE3), BL21 (DE3)pLysS, BL21 (DE3)pLysS (Studier (1991) J Mol Biol 219: 37-44), C41 (DE3) and C43 (DE3) are used (Miroux (1996) J Mol Biol 260, 289-98). In these strains, T7RNAP activity is fixed and the most suitable strain must be screened for overexpression of the desired protein. What strain will be best is something one cannot predict.

SUMMARY OF THE INVENTION

The inventors have shown that an adjustment of T7RNAP activity makes it easier for the host cell to couple transcription, translation and post-translational processes, and results in higher yields of functionally expressed protein and also reduces undesired aggregation of misfolded and mistargeted protein. Consequently, there is provided a novel system for the tunable expression of nucleic acids encoding e.g., polypeptides such as recombinant proteins in prokaryotic systems. The system is based on the ability of T7 lysozyme (T7Lys) to inhibit the activity of T7RNAP. Expression of T7Lys can be continuously adjusted as its expression is under the control of a promoter whose activity can be titrated, in particular T7Lys is operably linked to the rhaBAD promoter inducible by L-rhamnose (Giacalone, et al. (2006) Biotechniques 40:355-64). The core of the invention is a new vector expressible in a host comprising an adjustable promoter operably linked to the nucleic acid sequence encoding T7Lys. The said vector is not in the same incompatibility group as pET system or other T7 based expression vectors as it comprises origins of replication different from the colE1 origins of pBR1322 derived vectors, in particular the following origins of replication: p15A from pACYC, repA from pSC101, and cloDF13 from PCDF. This means that the new vector is capable of co-existing in the same cell as vectors of the pET system of other T7 based expression vectors. This enables the use of one strain for optimizing the expression conditions for a specific protein, and removes the need to screen for the most optimal strain.

*Escherichia coli* BL21 (DE3) transformed with a pACYC derived vector comprising the rhaBAD promoter operably linked to T7Lys is called Lemo21 (DE3). In this strain, T7Lys levels are regulated by the addition of L-rhamnose to the culture medium. T7Lys inhibits T7RNAP to a degree depending on the concentration of L-rhamnose. T7RNAP transcribes a recombinant target protein operably linked to a T7 promoter from a pET system vector. mRNA levels of the said recombinant protein are dependent on the activity of T7RNAP and thus on the concentration of L-rhamnose in the culture medium. Systems based on T7Lys operably linked to other titratable promoters work correspondingly. This includes the lactose [lac] (Yanisch-Perron et al., 1985, Gene 33, 103-109), and the tryptophan [trp] (Goeddel et al., 1980, Nature (London) 287, 411-416) promoters, and the hybrid promoters derived from these two [tac and trc] (Brosius, 1984, Gene 27: 161-172; Amann and Brosius, 1985, Gene 40, 183-190), the araB promoter inducible by arabinose (WO 86 04356), the rhamnose promoter rhaSB inducible by L-rhamnose (WO 03068956), and the tet promoter inducible by tetracyclin (Skerra (1994) Gene 151:131-5). Reduced mRNA levels enable *E. coli* to cope with overexpression stress, to continue growing, unaffected by the overexpression, and to finally yield more produced protein. The system according to the invention allows the inhibition of T7 RNA polymerase by T7 lysozyme in a continuously adjustable fashion to find the optimal expression conditions for each target protein. The system conveniently allows screening for optimal expression using only one strain rather than screening for optimal expression in different strains with fixed T7RNAP based expression intensities. The compatibility of our system with the widely used pET expression platform and other T7 based expression platforms offers an immense potential for the use of our product ranging from the small scale laboratory production of proteins to industry scale fermenter applications.

The invention further comprises the following aspects:

The present invention provides a host cell capable of expressing T7 RNA polymerase, the host cell comprising a first nucleic acid having a T7 lysozyme gene or a T7 lysozyme variant gene and a tunable promoter for controlling the expression of the T7 lysozyme gene or the T7 lysozyme variant gene.

In one embodiment, the invention provides a host cell as described above further comprising a second nucleic acid having a T7 promoter operably linked to a nucleic acid sequence encoding a target polypeptide, whereby expression of the target polypeptide is tuned via controlling the expression of the T7 lysozyme gene or the T7 lysozyme variant gene.

In another embodiment, the invention provides a host cell as described above, wherein said first nucleic acid comprising the tunable promoter is a first vector and said second nucleic acid comprising the T7 promoter is a second vector and wherein the first and the second vectors are compatible.

In another embodiment, the invention provides a host cell as described above, wherein said tunable promoter is tunable by rhamnose or arabinose.

In another embodiment, the invention provides a host cell as described above, wherein said tunable promoter is tunable by light.

In another embodiment, the invention provides a host cell as described above, wherein said tunable promoter is tunable by temperature.

In another embodiment, the invention provides a host cell as described above, wherein said first nucleic acid comprises a selection marker.

In another embodiment, the invention provides a host cell as described above, wherein the selection marker is an antibiotic selection marker.

In another embodiment, the invention provides a host cell as described above, wherein the variant of T7 lysozyme is LysY.

In another embodiment, the invention provides a host cell as described above, wherein said first nucleic acid is at least 80% identical to a nucleic acid chosen from the group comprising SEQ ID NO: 1-5.

In another embodiment, the invention provides a host cell as described above, wherein said first nucleic acid is substantially identical to a nucleic acid chosen from the group comprising SEQ ID NO: 1-5.

In another embodiment, the invention provides a host cell as described above, selected from the group of *E. coli, Pseudomonas aeruginosa, Erwinia carotovora, Salmonella choleraesuis, Agrobacterium tumefaciens, Chromobacterium violaceum, Lactococcus lactis, Bacillus subtilis, Salmonella, Saccharomyces cerevisiae, Pichia pastoris, Kluyveromyces lactis*, CHO, NS0, HEK293, HeLa, Sf9, tobacco, rice and *Leishmania tarentolae*.

In one aspect, the invention provides a method for producing a target polypeptide, comprising the steps of;
  a) providing a host cell as described above;
  b) inducing expression of the target polypeptide
  c) controlling the expression of the target polypeptide by tuning of said tunable promoter and thereby of the expression of said T7 lysozyme;
  and optionally
  d) isolating the polypeptide.

In one embodiment, the invention provides a method as described above, wherein the induction of expression of the target polypeptide is performed by inducing the expression of T7 RNA polymerase, or a variant thereof.

In another embodiment, the invention provides a method as described above, wherein the tuning of the tunable promoter, or a variant thereof, is accomplished by any of: light induction, temperature adjustment, addition of a chemical inducer, in particular rhamnose or arabinose.

In another aspect, the invention provides a nucleic acid comprising a T7 lysozyme gene or a T7 lysozyme variant gene and a tunable rhaBAD promoter for controlling the expression of the T7 lysozyme gene or the T7 lysozyme variant gene.

In one embodiment, the invention provides a nucleic acid as described above which is at least 80% identical to a nucleic acid chosen from the group SEQ ID NO: 1-5.

In another embodiment, the invention provides a nucleic acid as described above chosen from the group SEQ ID NO: 1-5.

The invention also provides use of the nucleic acid as described above for controlling the expression of a target polypeptide via T7 lysozyme.

BRIEF DESCRIPTION OF THE FIGURES

The invention will be further explained with reference to the accompanying drawings, in which.

DETAILED DESCRIPTION OF EMBODIMENTS

Figure 1:
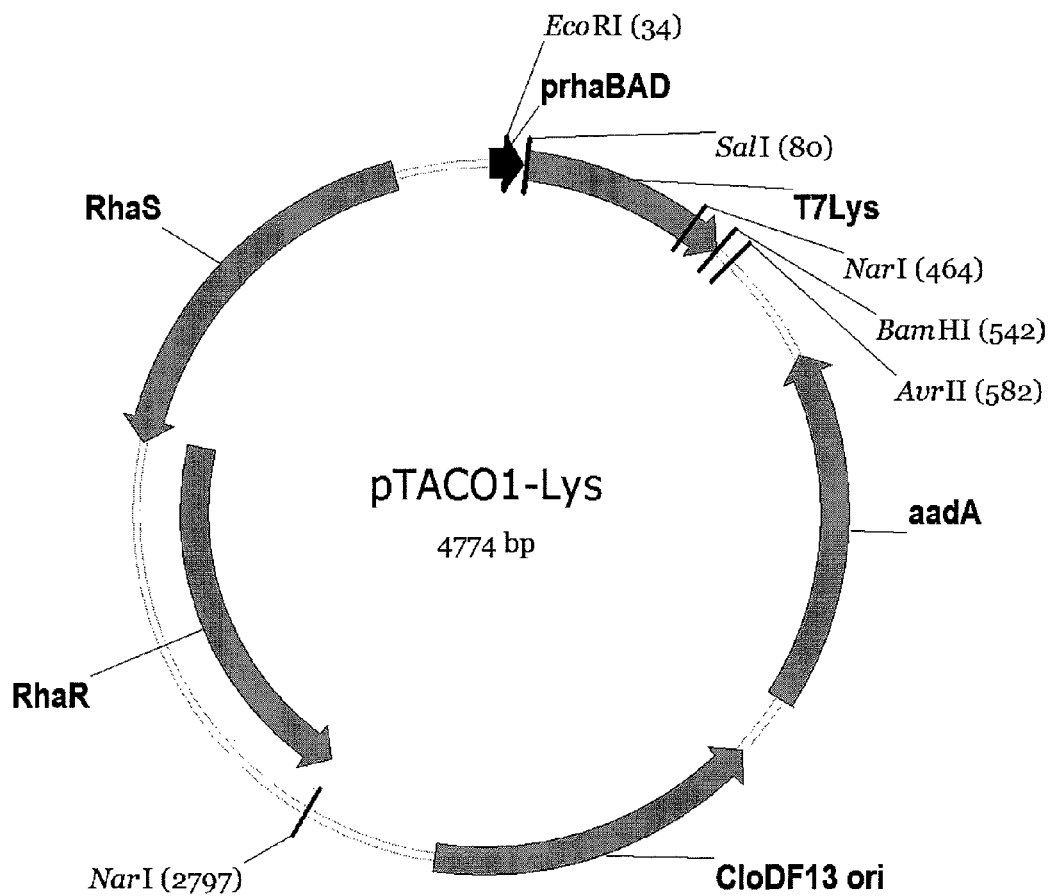
FIG. 1A-E shows maps of plasmids according to different embodiments of the invention, expressing T7 lysozyme or variants thereof from an L-rhamnose inducible promoter.
Figure 1:
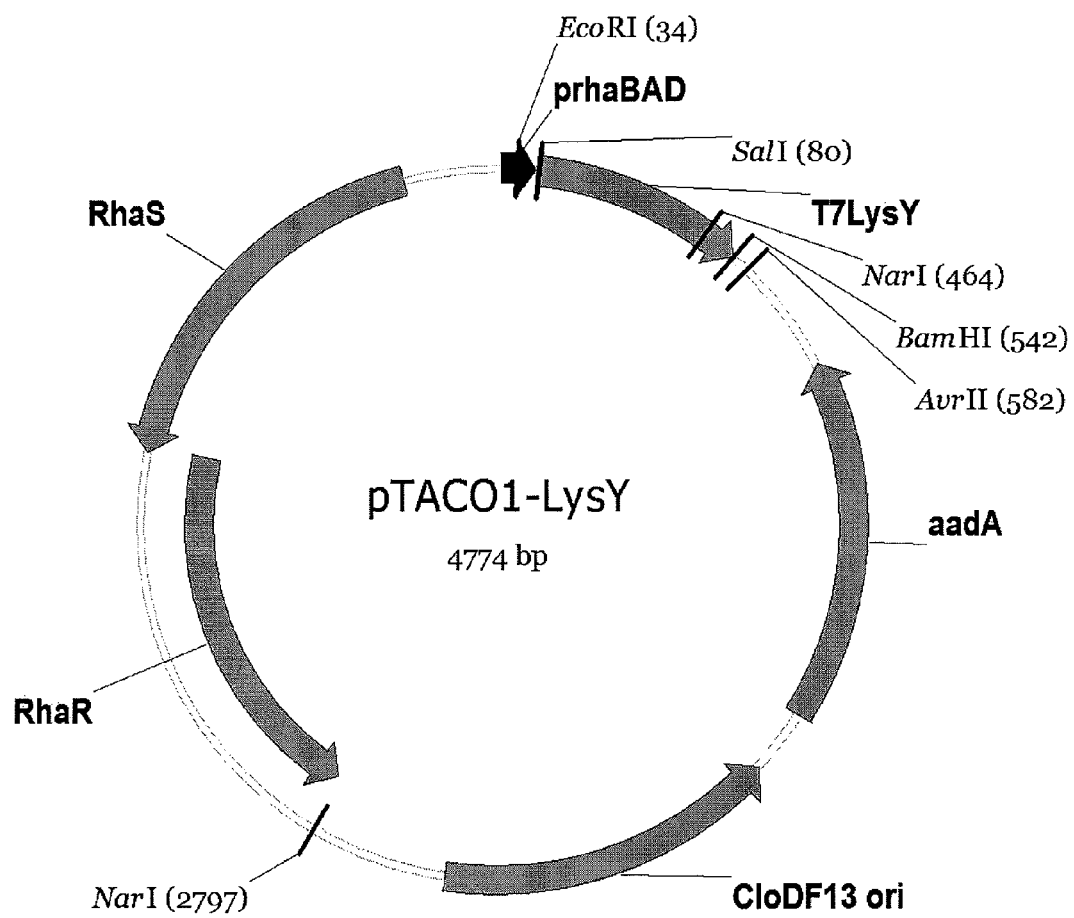
Figure 1:
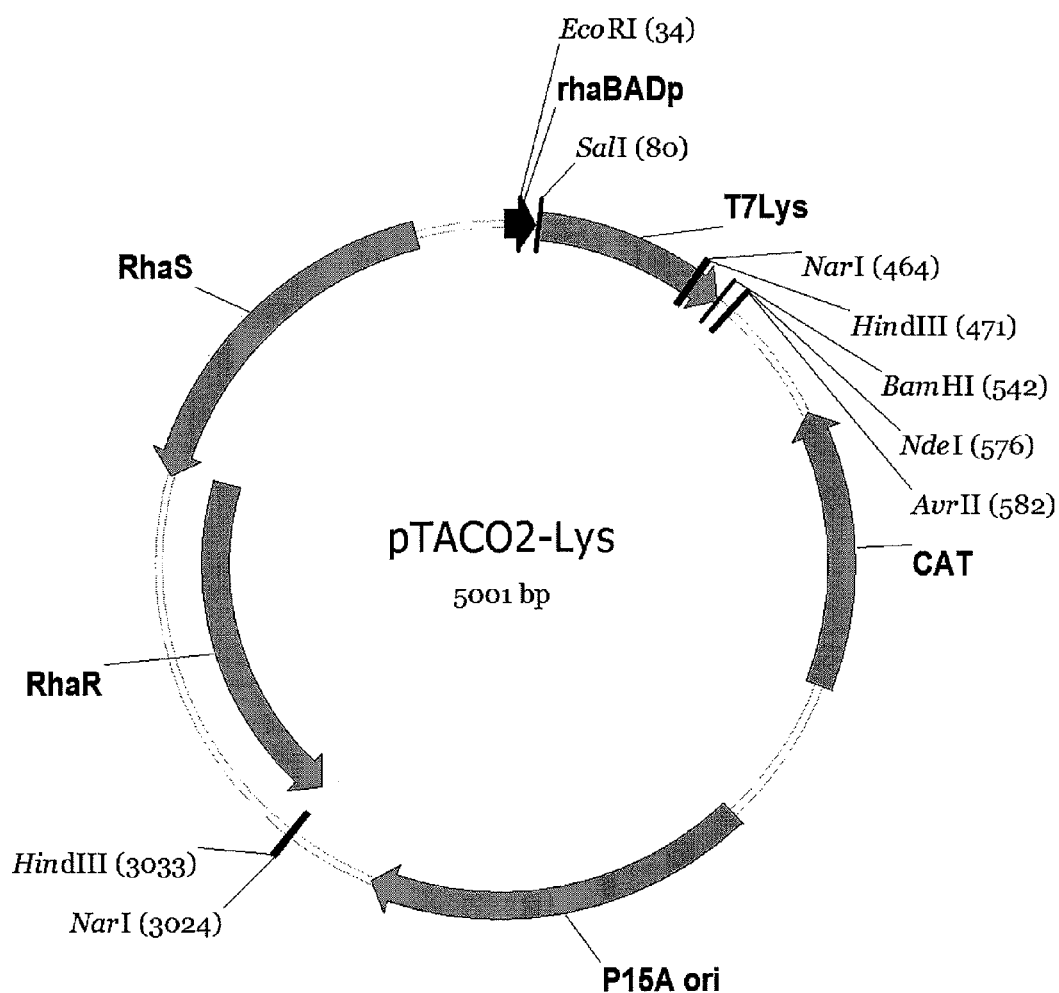
Figure 1:
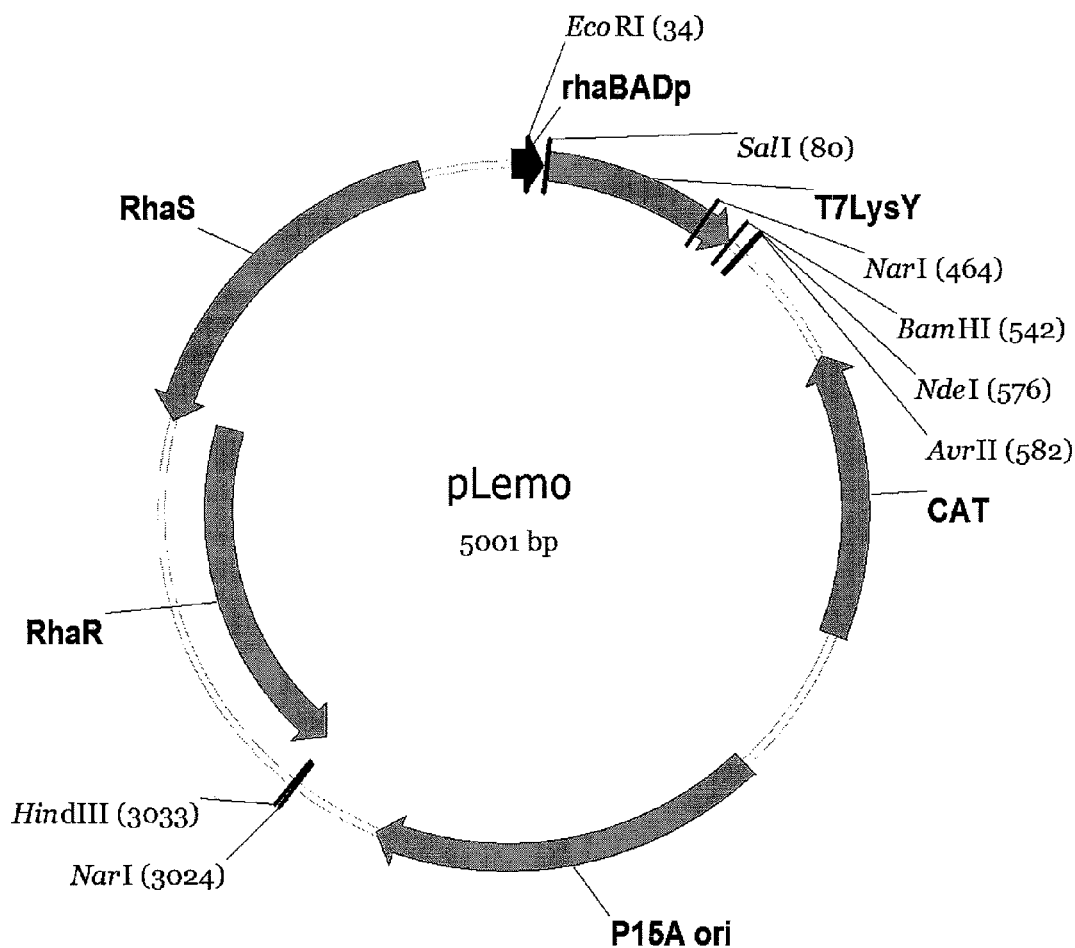
Figure 1:
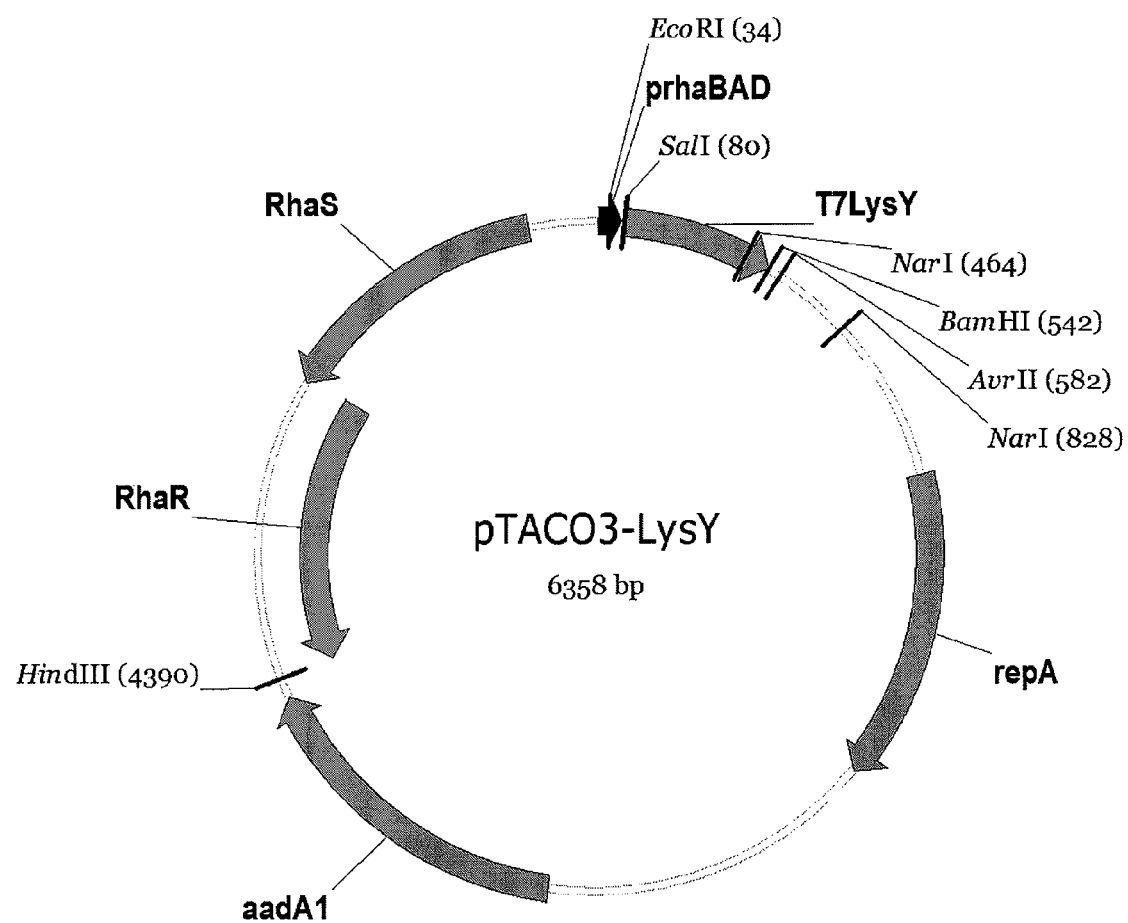

As used herein, the following definitions are supplied in order to facilitate the understanding of the present invention.

A "vector expressible in a host" or "expression vector" is a polynucleic acid construct, generated recombinantly or synthetically, with a series of specified polynucleic acid elements that permit transcription of a particular nucleic acid sequence in a host cell.

Typically, this vector includes a transcriptional unit comprising a particular nucleic acid sequence to be transcribed operably linked to a promoter. A vector expressible in a host can be e.g., an autonomously or self-replicating plasmid, a cosmid, a phage, a virus or a retrovirus.

The terms "host", "host cell" and "recombinant host cell" are used interchangeably herein to indicate a prokaryotic or eukaryotic cell into which one or more vectors or isolated and purified nucleic acid sequences of the invention have been introduced. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

"Promoter" as used herein refers to a nucleic acid sequence that regulates expression of a transcriptional unit. A "promoter region" is a regulatory region capable of binding RNA polymerase in a cell and initiating transcription of a downstream (3' direction) coding sequence. Within the promoter region will be found a transcription initiation site (conveniently defined by mapping with nuclease S 1), as well as protein binding domains (consensus sequences) responsible for the binding of RNA polymerase such as the putative −35 region and the Pribnow box.

An "adjustable promoter" is a promoter whose effect on expression of a transcriptional unit depends on the concentration of an inducer (if a chemical compound is the inducer) or the intensity of an inducer (if light or temperature is the inducer). Lower inducer concentrations result in a lower rate of transcription (rate of transcription; number of mRNA molecules synthesized per unit of time) and higher inducer concentrations result in a higher rate of transcription.

The terms "regulatable", "controllable", "titratable", "adjustable" and "tunable" are to be used synonymously "L-rhamnose operon" refers to the rhaSR-rhaBAD operon as described for $E.$ $coli$ in Hoicroft and Egan, 2000, J. Bacteriol. 182 (23), 6774-6782. The rhaBAD operon is a positively regulated catabolic operon which transcribes RhaB, RhaA and RhaD divergently from another rha operon, rhaSR, with approximately 240 bp of DNA separating their respective transcription start sites. The rhaSR operon encodes the two L-rhamnose-specific activators RhaS and RhaR. RhaR regulates transcription of rhaSR, whereas RhaS bind DNA upstream at −32 to −81 relative to the transcription start site of rhaBAD. Furthermore, the rhaSR-rhaBAD intergenic operon contains CRP binding sites at positions −92.5 (CRP 1) relative to the transcription start site of rhaBAD and CRP binding sites at positions −92.5 (CRP 2), −115.5 (CRP 3) and −116.5 (CRP 4) relative to the transcription start site of rhaSR as well as a binding site for RhaR spanning −32 to −82 relative to the transcription start site of rhaSR. With "rhaBAD promoter region of the L-rhamnose operon" is meant the rhaBAD operon comprising essentially of the rhaJBAD transcription initiation site, the putative −35 region, the Pribnow box, the CRP binding site CPRI, the binding site for RhaS relative to the transcription start site of rhaBAD as well as CRP binding sites CRP 2-4, and binding site for RhaR relative to the transcription start site o[iota]rhaSR. With "rhaBAD promoter" is meant the promoter of the rhaBAD operon comprising essentially of the rhaBAD transcription initiation site, the putative −35 region, the Pribnow box, the binding site for RhaS and the CRPI binding site region relative to the transcription start site of rhaBAD, and the CRP binding site CRP4 or a part thereof relative to the transcription start site of rhaSR.

"CRP" means "Catabolite regulator protein". "CRP" is often referred in the art as "cyclic AMP receptor protein", which has the synonymous meaning. CRP is a regulator protein controlled by cyclic AMP (cAMP) which mediates the activation of catabolic operons such as the L-rhamnose operon.

An "enhancer" is a nucleic acid sequence that acts to potentiate the transcription of a transcriptional unit independent of the identity of the transcriptional unit, the position of the sequence in relation to the transcriptional unit, or the orientation of the sequence. The vectors of the present invention optionally include enhancers.

"Transcriptional unit" as used herein refers to a nucleic acid sequence that is normally transcribed into a single RNA molecule. The transcriptional unit might contain one gene (monocistronic) or two (dicistronic) or more genes (polycistronic) that code for functionally related polypeptide molecules.

A nucleic acid sequence is "operably linked" when it is placed into a functional relationship with another nucleic acid sequence. For example, a promoter is operably linked to a coding sequence if it affects the transcription of the sequence; or a translation initiation region such as a ribosome binding site is operably linked to a nucleic acid sequence encoding e.g., a polypeptide if it is positioned so as to facilitate translation of the polypeptide. Linking can be accomplished by ligation at convenient restriction sites. If such sites do not exist, the synthetic oligonucleotide adaptors or linkers are used in accordance with conventional practice.

"Nucleic acid" or "nucleic acid sequence" or "isolated and purified nucleic acid or nucleic acid sequence" as referred in the present invention might be DNA, RNA, or DNA/RNA hybrid. In case the nucleic acid or the nucleic acid sequence is located on a vector, it is usually DNA. DNA which is referred to herein can be any polydeoxynucleotide sequence, including, e.g., double-stranded DNA, single-stranded DNA, double-stranded DNA wherein one or both strands are composed of two or more fragments, double-stranded DNA wherein one or both strands have an uninterrupted phosphodiester backbone, DNA containing one or more single-stranded portion(s) and one or more double-stranded portion(s), double-stranded DNA wherein the DNA strands are fully complementary, double-stranded DNA wherein the DNA strands are only partially complementary, circular DNA, covalently—closed DNA, linear DNA, covalently cross-linked DNA, cDNA, chemically—synthesized DNA, semi-synthetic DNA, biosynthetic DNA, naturally-isolated DNA, enzyme-digested DNA, sheared DNA, labeled DNA, such as radiolabeled DNA and fluorochrome-labeled DNA, DNA containing one or more non-naturally occurring species of nucleic acid. DNA sequences can be synthesized by standard chemical techniques, for example, the phosphotriester method or via automated synthesis methods and PCR methods. The purified and isolated DNA sequence may also be produced by enzymatic techniques.

A "substantially identical" sequence is a nucleotide sequence that differs from a reference sequence only by one or more conservative substitutions, as discussed herein, or by one or more non-conservative substitutions, deletions, or insertions located at positions of the sequence that do not destroy the biological function of the nucleic acid molecule.

Such a sequence can be any value from 10% to 99%, or more generally at least 10%, 20%, 30%, 40%, 50, 55% or 60%, or at least 65%, 75%, 80%, 85%, 90%, or 95%, or as much as 96%, 97%, 98%, or 99% identical when optimally aligned at the amino acid or nucleotide level to the sequence used for comparison using, for example, the Align Program 18 or FASTA. The length of comparison sequences may be at least 5, 10, 15, 20, or 25 nucleotides, or at least 30, 40, or 50 nucleotides. In alternate embodiments, the length of comparison sequences may be at least 60, 70, 80, or 90 nucleotides, or over 100, 200, or 500 nucleotides.

Sequence identity can be readily measured using publicly available sequence analysis software (e.g., Sequence Analysis Software Package of the Genetics Computer Group, University of Wisconsin Biotechnology Center, 1710 University Avenue, Madison, Wis; 53705, or BLAST software available from the National Library of Medicine, or as described herein). Examples of useful software include the programs Pile-up and PrettyBox. Such software matches similar sequences by assigning degrees of homology to various substitutions, deletions, substitutions, and other modifications. Substantially identical sequences include homologous sequences, such as COPI related sequences from non-human species as described herein or known in the art.

Alternatively, or additionally, two nucleic acid sequences may be "substantially identical" if they hybridize under high stringency conditions. In some embodiments, high stringency conditions are, for example, conditions that allow hybridization comparable with the hybridization that occurs using a DNA probe of at least 500 nucleotides in length, in a buffer containing 0.5 M $NaHPO_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. (These are typical conditions for high stringency northern or Southern hybridizations.) Hybridizations may be carried out over a period of about 20 to 30 minutes, or about 2 to 6 hours, or about 10 to 15 hours, or over 24 hours or more. High stringency hybridization is also relied upon for the success of numerous techniques routinely performed by molecular biologists, such as high stringency PCR, DNA sequencing, single strand conformational polymorphism analysis, and in situ hybridization. In contrast to northern and Southern hybridizations, these techniques are usually performed with relatively short probes (e.g., usually about 16 nucleotides or longer for PCR or sequencing and about 40 nucleotides or longer for in situ hybridization). The high stringency conditions used in these techniques are well known to those skilled in the art of molecular biology, and examples of them can be found, for example, in Ausubel et al., 1994, Current Protocols in Molecular Biology, John Wiley and Sons.

RNA which is referred to herein can be e.g., single-stranded RNA, cRNA, double-stranded RNA, double-stranded RNA wherein one or both strands are composed of two or more fragments, double-stranded RNA wherein one or both strands have an uninterrupted phosphodiester backbone, RNA containing one or more single-stranded portion(s) and one or more double-stranded portion(s), double-stranded RNA wherein the RNA strands are fully complementary, double-stranded RNA wherein the RNA strands are only partially complementary, covalently crosslinked RNA, enzyme-digested RNA, sheared RNA, mRNA, chemically-synthesized RNA, semi-synthetic RNA, biosynthetic RNA, naturally-isolated RNA, labeled RNA, such as radiolabeled RNA and fluorochrome-labeled RNA, RNA containing one or more non-naturally—occurring species of nucleic acid.

With "variants" or "variants of a sequence" or "variant gene" is meant a nucleic acid sequence that vary from the reference sequence by conservative nucleic acid substitutions, whereby one or more nucleic acids are substituted by another with same characteristics. Variants encompass as well degenerated sequences, sequences with deletions and insertions, as long as such modified sequences exhibit the same function (functionally equivalent) as the reference sequence.

As used herein, the terms "polypeptide", "peptide", "protein", "polypeptidic" and "peptidic" are used interchangeably to designate a series of amino acid residues connected to the other by peptide bonds between the alpha-amino and carboxy groups of adjacent residues.

The term "isolated and purified nucleic acid sequence" refers to the state in which the nucleic acid sequence will be, in accordance with the present invention. The nucleic acid sequence will be free or substantially free of material with which they are naturally associated such as other nucleic acids with which they are found in their natural environment, or the environment in which they are prepared (e.g., cell culture) when such preparation is by recombinant technology practiced in vitro or in vivo.

The terms "transformation", "transformed" or "introducing a nucleic acid into a host cell" denote any process wherein an extracellular nucleic acid like a vector, with or without accompanying material, enters a host cell. The term "cell transformed" or "transformed cell" means the cell or its progeny into which the extracellular nucleic acid has been introduced and thus harbours the extracellular nucleic acid. The nucleic acid might be introduced into the cell so that the nucleic acid is replicable either as a chromosomal integrant or as an extra chromosomal element. Transformation of appropriate host cells with e.g., an expression vector can be accomplished by well known methods such as microinjection, electroporation, particle bombardment or by chemical methods such as Calcium phosphate-mediated transformation, described e.g., in Maniatis et al. 1982, Molecular Cloning, A laboratory Manual, Cold Spring Harbor Laboratory or in Ausubel et al. 1994, Current protocols in molecular biology, John Wiley and Sons.

"Heterologous nucleic acid sequence" or "nucleic acid sequence heterologous to a host" means a nucleic acid sequence which encodes e.g., an expression product such as a polypeptide that is foreign to the host ("heterologous expression" or "heterologous product") i.e., a nucleic acid sequence originating from a donor different from the host or a chemically synthesized nucleic acid sequence which encodes e.g., an expression product such as a polypeptide that is foreign to the host. In case the host is a particular prokaryotic species, the heterologous nucleic acid sequence is preferably originated from a different genus or family, more preferred from a different order or class, in particular from al different phylum (division) and most particular from a different domain (empire) of organisms.

"Homologous nucleic acid sequence or "nucleic acid sequence homologous to a host" means a nucleic acid sequence which encodes e.g., an expression product such as a polypeptide that is from the host ("homologous expression" or "homologous product") i.e., a nucleic acid sequence originating from the host or a chemically synthesized nucleic acid sequence which encodes e.g., an expression product such as a polypeptide that is from the host.

The heterologous nucleic acid sequence originating from a donor different from the host can be modified, before it is introduced into a host cell, by mutations, insertions, deletions or substitutions of single nucleic acids or a part of the heterologous nucleic acid sequence as long as such modified sequences exhibit the same function (functionally equivalent) as the reference sequence. A heterologous nucleic acid sequence as referred herein encompasses as well nucleic acid sequences originating from a different domain (empire) of organisms such as from eukaryotes (of eukaryotic origin) such as e.g., human antibodies which have been used in phage display libraries and of which single nucleic acids or a part of the nucleic acid sequences have been modified according to the "codon usage" of a host.

"Translation initiation region" is a signal region which promotes translation initiation and which functions as the ribosome binding site such as the Shine Dalgarno sequence.

"Transcription termination region" refers to a sequence which causes RNA polymerase to terminate transcription. The transcription termination region is usually part of a transcriptional unit and increases the stability of the mRNA.

The vector according to the invention is preferably an autonomously or self-replicating plasmid, a cosmid, a phage, a virus or a retrovirus. A wide variety of host/vector combinations maybe employed in expressing the nucleic acid sequences of this invention. Useful expression vectors, for example, may comprise of segments of chromosomal, non-chromosomal and/or synthetic nucleic acid sequences. Suitable vectors include vectors with specific host range such as vectors specific for e.g., E. coli as well as vectors with broad-host-range such as vectors useful for Gram-negative or Gram-positive bacteria. "Low-copy", "medium-copy" as well as "high copy" plasmids can be used.

Useful vectors for e.g., expression in E. coli are: pQE70, pQE60 und pQE-9 (QIAGEN, Inc.); pBluescript vectors, Phagescript vectors, pNH8A, [rho]NH16a, pNH18A, [rho]NH46A (Stratagene Cloning Systems, Inc.); ptrc99a, pKK223-3, [rho]KK233-3, pDR540, pRIT5 (Pharmacia Biotech, Inc.); pLG338, pACYC184, pBR322, pUC18, pUC19, pKC30, pRep4, pACYC177, pACYC184, pRSFIOIO and pBW22 (Wilms et al., 2001, Biotechnology and Bioengineering, 73 (2) 95-103) or derivates thereof. Further useful plasmids are well known to the person skilled in the art and are described e.g., in "Cloning Vectors" (Eds. Pouwels P. H. et al. Elsevier, Amsterdam-New York-Oxford, 1985).

Preferred vectors of the present inventions are autonomously or self-replicating plasmids, more preferred are vectors with specific host range such as vectors specific for e.g., E. coli. Most preferred are pBR322, pUC18, pACYC177, pACYC184, pRSFIOIO and pBW22 or derivates thereof.

In a preferred embodiment, the rhaBAD promoter region of the L-rhamnose operon, or a functionally equivalent variant thereof, is the adjustable promoter. The transcription from the rhaBAD promoter is extremely well regulated and tightly controlled by the rhamnose concentration of the cell culture medium. By tuning the rhamnose concentration of the culture medium the activity of the rhaBAD promoter can thus be very well controlled. The rhaBAD promoter also covers a broad window of expression intensities. In a particular preferred embodiment, the rhaBAD promoter consists of the sequence gcccattttcctgtcagtaacgagaag-gtcgcgaattcaggcgcttttagactggtcgtaatgaaattcag (SEQ ID NO: 6), or a sequence complementary thereto and variants thereof. A variant of the promoter useful in the invention is one capable of performing essentially the same functions as the original promoter, in particular direct transcription by way of an RNA polymerase. In another preferred embodiment the adjustable promoter is the araBAD promoter or a functionally equivalent variant thereof.

In another preferred embodiment of the invention the vector expressible in a prokaryotic host comprises apart from the rhaBAD promoter region of the L-rhamnose operon operably linked to a transcriptional unit furthermore sequences encoding the L-rhamnose-specific activators RhaS and RhaR including their respective native promoter sequences. Upon expression the RhaS and RhaR proteins: control the activity of the rhaBAD promoter.

A "biological membrane", "biomembrane" or merely "membrane" is an enclosing or separating amphipathic layer that acts as a barrier within or around a cell. It is, almost invariably, a lipid bilayer, composed of a double layer of lipid-class molecules, specifically phospholipids, with occasional proteins intertwined.

A "transmembrane protein" or "integral membrane protein" is a protein that spans the entire biological membrane. Transmembrane proteins aggregate and precipitate in water. They require detergents or nonpolar solvents for extraction, although some of them (beta-barrels) can be also extracted using denaturing agents. There are two basic types of transmembrane proteins: a) Alpha-helical. These proteins are present in all types of biological membranes including outer membranes. This is the major category of transmembrane proteins. b) Beta-barrels. These proteins are found only in outer membranes of Gram-negative bacteria, cell wall of Gram-positive bacteria, and outer membranes of mitochondria and chloroplasts.

An "inner membrane protein" is a protein that resides, at least in part, in the inner membrane of a Gram-negative bacterium, such as E. coli. An integral inner membrane protein is typically alpha-helical.

An "outer membrane protein" is a protein that resides, at least in part, in the outer membrane of a Gram-negative bacterium, such as E. coli. An integral outer membrane protein is typically a beta-barrel.

A "secreted protein" or "secretory protein" refers to a protein that is translocated through at least one biomembrane.

The lysozyme of bacteriophage T7 (T7 lysosozyme) is a bifunctional protein that cuts amide bonds in the bacterial cell wall and binds to and inhibits transcription by T7 RNA polymerase. (Moffatt and Studier (1987) Cell 49:221-7; Jeruzalmi and Steitz (1998) EMBO J. 14: 4101-13; Cheng, et al. (1994) Proc Natl Acad Sci USA 91:4034-8). These functions are not separated into independent domains, and an individual molecule is able to perform only one function at a time (Jeruzalmi and Steitz (1998) EMBO J. 14: 4101-13). Binding of T7 lysozyme to the T7 RNA polymerase locks the T7 RNA polymerase in a nonprocessive state, thereby reducing initiation of RNA chains from phage promoters (Jeruzalmi and Steitz (1998) EMBO J. 14: 4101-13). There are mutants of T7Lys that lack amidase activity but still can bind and inhibit T7RNAP (Cheng, et al. (1994) Proc Natl Acad Sci USA 91:4034-8). Examples of amidase deficient mutants of T7 lysozyme that retain T7 RNA polymerase inhibitory activity are: Y46F, K128Q, K128W, K128Y, K128M, K128I (Cheng, et al. (1994), Proc Natl Acad Sci USA 91:4034-8). "T7 lysozyme variant genes" i.e. both wild type and mutant forms of the T7Lys that retain T7 RNA polymerase inhibition activity may be used in this invention. The T7 lysozyme K128Y mutant is also referred to as LysY. T7 RNA polymerase is the RNA polymerase encoded by bacteriophage T7. Also mutants of T7RNA polymerase (Makarova, et al. (1995) Proc Natl Acad Sci USA 92:12250-4) may be used.

T7 promoters are the promoters recognized by T7 RNA polymerase (Chamberlin et al., (1970) Nature 228, 227-231; Oakley and Coleman (1977) PNAS 74, 4266-4270; Rosa (1979) Cell 16, 815-825; Panayotatos and Wells (1979) Nucl. Acids Res. 13, 2227-2240; Dunn and Studier (1983) J. Mol. Biol. 166, 477-535/175, 111-112). The φ10 Promoter is most often used in T7 expression systems and usually referred to as 'T7 promoter'. The lac operator can be operationally linked to a T7 promoter (T7/lac fusion promoter or T7lac), which helps to control basal expression in an inducible T7 expression system by blocking the target T7 promoter with lac repressor (Dubendorff and Studier (1991) J Mol Biol 219:45-59). The T7lac promoter is usually also referred to as 'T7 promoter'.

The T7 system is the most widely used system to produce recombinant proteins in Escherichia coli. Target genes are cloned in pET or other T7 system plasmids under control of a T7 promoter; expression is induced by providing a source of T7 RNA polymerase in the host cell.

The expression "recombinant mRNA" refers to the mRNA encoding for a polypeptide to be produced.

The expression "inducer" refers to a small molecule that can increase the transcription of an operon. It also refers to other signals that can increase the transcription of an operon such as light or temperature.

The origin of replication (also called the replication origin) is a particular DNA sequence at which DNA replication is initiated. DNA replication may proceed from this point bidirectionally or unidirectionally.

An "incompatibility (inc) group" is a set of plasmids that interfere with each other's replication and/or partitioning and so cannot be stably maintained together in the same culture.

The expression "plasmid copy number" refers to the average number of a particular plasmid per cell. The plasmid copy number is determined by the origin of replication.

The expression "target protein" refers to a recombinant protein that is to be overexpressed. The nucleic acid sequence encoding for the recombinant protein is operably linked to a T7 promoter or a T7/lac fusion promoter or other derivatives of that kind. The target protein can be: a) a heterologous or homologous protein, b) a soluble cytoplasmic, soluble secretory or membrane protein. In particular, the target protein is any protein with complex post-translational requirements. More specifically, the target protein requires a) targeting to the membrane, insertion into the membrane or translocation through the membrane, or b) post-translational modifications, insertions of prosthetic groups or the formation of chromophores. Most specifically, the target protein is an integral membrane protein or a secretory protein, a protein that is post-translationally modified or a protein that requires assistance of chaperone(s) for its folding.

"Overexpression" and "production" are to be used synonymously.

An "antibiotic resistance marker" or "selection marker", is a fragment of DNA that contains a gene whose product confers resistance to an antibiotic (e.g., chloropamphenicol, ampicillin, gentamycin, streptomycin, tetracyclin, kanamycin, neomycin) or the ability to grow on selective media (e.g., ura (uracil), leu (leucine), trp (tryptophan), his (histidine). The strains used are auxotrophic mutants that cannot make the above mentioned molecules. The vector contains the gene that can convert an auxotroph into a non-auxotroph, i.e., the vector (after transformation) makes it possible for a cell to grow on medium lacking the molecule(s) it was not able to grow on before transformation (Amberg et al. (2005) Methods in Yeast Genetics. Cold Spring Harbor Laboratory Press). Usually, plasmids contain antibiotic resistance marker to force the bacterial cell to maintain the plasmid.

Figure 2:
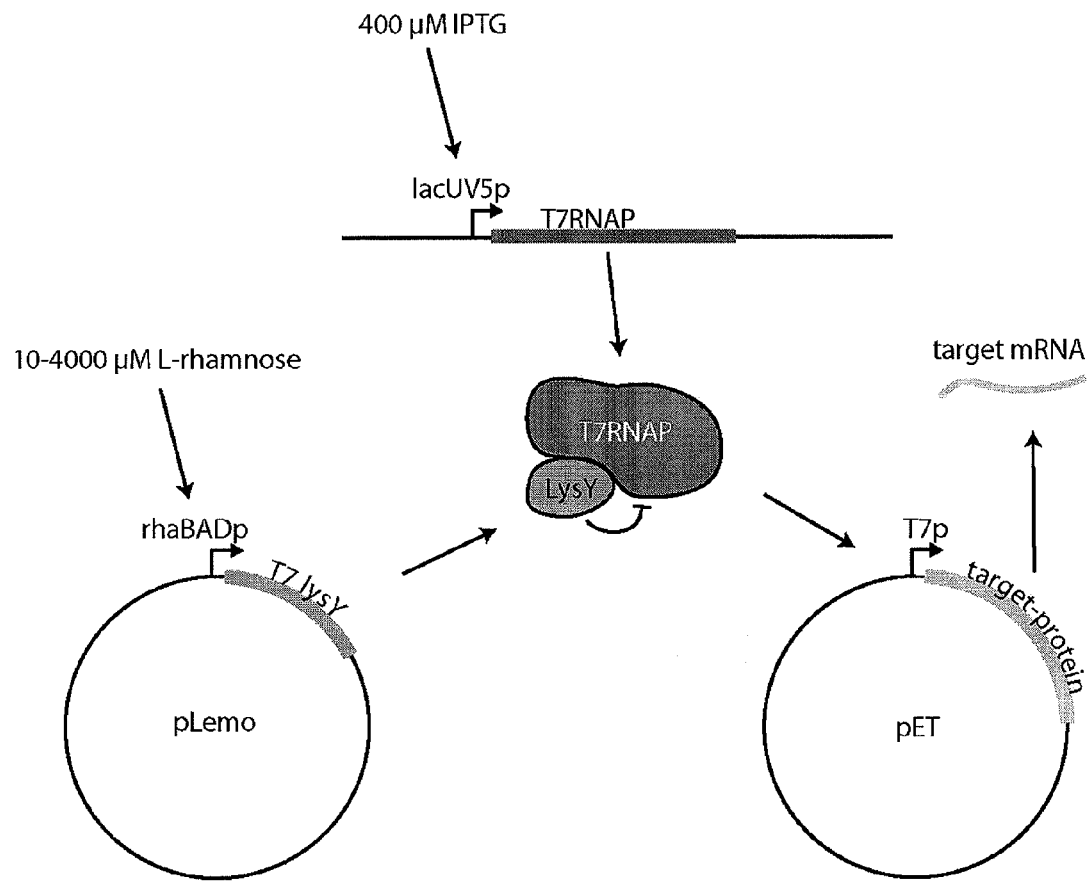
FIG. 2 shows a model of the control of T7 RNA polymerase activity by titration of T7 lysozyme expression, according to an embodiment of the present invention.

One embodiment of the present invention is schematically shown in FIG. 2. Host cells are transformed with a vector comprising a tunable promoter, exemplified by the rhaBAD promoter, operably linked to T7 Lysozyme. In these host cells, T7 Lysozyme levels are regulated by the addition of L-rhamnose to the culture medium in a tightly correlated manner, where increasing concentrations of L-rhamnose lead to increasing levels of T7 Lysozyme. T7 Lysozyme inhibits T7 RNA polymerase (T7RNAP) to a degree depending on the concentration of L-rhamnose. T7RNAP transcribes a recombinant target protein operably linked to a T7 promoter from e.g. a pET system vector. mRNA levels of the said recombinant protein are dependent on the activity of T7RNAP and thus on the concentration of L-rhamnose in the culture medium. Reduced mRNA levels enable E. coli to cope with overexpression stress, to continue growing, unaffected by the overexpression, and to finally yield more produced protein. The system according to the invention allows the inhibition of T7 RNA polymerase by T7 lysozyme in a continuously adjustable fashion to find the optimal expression conditions for each target protein.

T7 lysozyme inhibits T7 RNA polymerase. The amount of T7 lysozyme relative to the amount of T7 RNA polymerase determines the degree of inhibition. In one aspect, the present invention provides a vector expressible in a host comprising the rhaBAD promoter region of the L-rhamnose operon operably linked to a nucleic acid sequence encoding T7 lysozyme. Said vector has to be stably maintained in the host by the help of e.g., a selection marker.

More specifically, T7 lysozyme is expressed from a plasmid. Said plasmid comprises a gene encoding for T7 lysozyme operably linked to the adjustable promoter, an antibiotic resistance marker and an origin of replication that is preferably not in the same incompatibility group as plasmids containing the ColE1 origin of replication. In a preferred embodiment said adjustable promoter is the rhaBAD promoter, inducible by L-rhamnose, and said plasmid also preferably comprises the rhaSR operon encoding the two L-rhamnose-specific activators RhaS and RhaR. In another embodiment the adjustable promoter is the araBAD promoter. More specifically, T7 lysozyme is preferably expressed from plasmids pLEMO (SEQ ID NO:1, also denoted <400> 1), pTACO1-Lys (SEQ ID NO:2, also denoted <400> 2), pTACO1-LysY (SEQ ID NO:3, also denoted <400> 3), pTACO2-Lys (SEQ ID NO:4, also denoted <400> 4), pTACO3-Lys or pTACO3-LysY (SEQ ID NO:5, also denoted <400> 5). Said plasmids have the sequences given below. pTACO1 comprises a cloDF13 origin of replication and a spectinomycin resistance marker; pTACO1-LysY comprises a cloDF13 origin of replication and a spectinomycin resistance marker and codes for the mutant LysY; pTACO2 and pLEMO comprise a P15A origin of replication and a chloramphenicol resistance marker and pTACO3 comprises a pSC101 derived repA origin of replication and a spectinomycin resistance marker. The said plasmids may be made synthetically or by recombinant techniques, which, along all other molecular technologies may be performed as described in Maniatis et al. 1982, Molecular Cloning, A laboratory Manual, Cold Spring Harbor Laboratory or in Ausubel et al. 1994, Current protocols in molecular biology, John Wiley and Sons.

A target protein is to be expressed from an expression vector. Said vector has to be stably maintained in the host by the help of e.g., a selection marker. In particular, the target protein is to be expressed from a T7 system plasmid.

A host cell is to be transformed with a) a vector comprising a gene encoding for T7 lysozyme operably linked to an adjustable promoter and b) a vector comprising a gene encoding for a target protein operably linked to a T7 promoter, preferably, the target protein is encoded on a T7 system plasmid.

In a commercially advantageous embodiment of the present invention the host cell may be sold carrying only the vector comprising a gene encoding for T7 lysozyme. The vector is constructed so as to be compatible with commercially available expression vectors, such as pET-vectors, designed to carry a gene encoding a target protein (gene of interest) operably linked to a T7 promoter. Such a commercially available vector, having the gene encoding for a specific target protein, may thus be available or constructed at the customer's site, and transformed into the host cell of the present invention at that site.

The genome of said host comprises a promoter operably linked to a nucleic acid sequence encoding for T7 RNA polymerase. In particular, the genome of said host comprises an IPTG inducible lac promoter or one of its derivatives such as the lacUV5 mutant promoter, operably linked to a nucleic acid sequence encoding for T7 RNA polymerase. In particular, the host is Escherichia coli strain BL21 (DE3) or any other host capable of expressing the T7 RNA polymerase.

According to the invention, other preferred promoters for inducing the T7 lysozyme include the Tet promoter, which is induced by anhydrotetracycline, and has the sequence TTGACACTCTATCATTGATAGAGTTATTTTACCACT, SEQ ID NO:13;

the araBAD promoter, which is induced by arabinose, and has the sequence

```
                                      SEQ ID NO: 14
CCATAAGATTAGCGGATCCTACCTGACGCTTTTTATCGCAACTCTCTACT

GTTTCTCCATACCCGTTTTTTTGGATGGAGT,;
``` and the rhaBAD promoter, which is induced by L-rhamnose, and has the sequence

```
                                      SEQ ID NO: 15
GCCCATTTTCCTGTCAGTAACGAGAAGGTCGCGAATTCAGGCGCTTTTTA

GAGTGGTCGTAATGAAATTCAGCAGGATCAC,.
```

A host comprising a) a vector comprising an adjustable promoter operably linked to a nucleic acid sequence encoding for T7 lysozyme, b) a promoter operably linked to a nucleic acid sequence encoding T7 RNA polymerase and c) a T7 promoter operably linked to a nucleic acid sequence encoding for a target protein is normally grown under standard conditions with regards to temperature in standard culture medium.

Host cells are usually cultured in conventional media as known in the art such as complex media like Luria-Broth or "nutrient yeast broth medium" or a glycerol containing medium as described by Kortz et al., 1995, J. Biotechnol. 39, 59-65 or a mineral salt media as described by Kulla et al., 1983, Arch. Microbiol, 135, 1. The medium might be modified as appropriate e.g., by adding further ingredients such as buffers, salts, vitamins or amino acids. As well different media or combinations of media can be used during the culturing of the cells. Preferably, the medium used as basic medium should not include L-rhamnose, in order to achieve a tight regulation of the L-rhamnose promoter region.

If the host is Escherichia coli BL21 (DE3), an over night culture of said host is backdiluted to an $A_{600}$ of 0.01 to 0.05. The culture medium is supplemented with an inducer inducing the expression of T7 lysozyme from the adjustable promoter. In particular the culture medium is supplemented with 10 µM to 10 mM L-rhamnose to induce the expression of T7 lysozyme from the rhaBAD promoter. The concentration of L-rhamnose in the culture medium determines the expression of T7 lysozyme which determines the inhibition of T7 RNA polymerase and hence expression of said target protein and concentration of recombinant mRNA in the host cell.

When the culture of said host is at an $A_{600}$ of 0.4 to 0.5, expression of the target protein is induced by the addition of inducer to the culture medium, in particular by the addition of 0.01 to 10.0 mM IPTG, more specifically, by the addition of 0.1-1 mM IPTG. Inducer induces the expression of T7 RNA polymerase which binds to the T7 promoter operably linked to the nucleic acid sequences encoding the target protein and transcribes the target protein. T7 RNA polymerase activity depends on the concentration of T7 lysozyme in the host cell. The amount of transcribed mRNA depends on the activity of T7 RNA polymerase.

The expression of the target protein is monitored after induction of expression. The concentration of inducer, in particular of L-rhamnose, that yields the highest amount of target protein is chosen for expression of the target protein.

This can be monitored by e.g., SDS-PAGE combined with Coomassie/silver staining, Western-blotting or variants thereof like dot blotting (methods available at the Cold Spring Harbor Protocols website). If Green Fluorescent Protein (GFP) is fused to the overexpressed protein also whole cell and in-gel fluorescence can be used to monitor expression of the target protein. When a membrane protein is fused to GFP, GFP is only fluorescent when the fusion is expressed in the membrane and not in inclusion bodies/aggregates (Drew et al., Protein Sci. (2005) 8, 2011-7; Drew et al., Nat. Methods (2006) 4, 303-13).

The concentration of inducer for the induction of expression of T7 lysozyme can be chosen in such a way that the rate of produced recombinant mRNA and hence the rate of produced recombinant target protein is optimal for post-translational biogenesis of the recombinant target protein. For example, in regard of a membrane protein toxic effects of its overexpression can be minimized by harmonizing translation and insertion into the membrane, and in regard of a protein requiring chaperone assistance for appropriate folding the rate of recombinant target protein production can be set to allow available chaperone(s) to keep up with the folding workload (i.e., chaperone capacity is sufficient to assist folding of the overexpressed protein).

As cell culture systems, continuous or discontinous culture such as batch culture or fed batch culture can be applied in culture tubes, shake flasks or bacterial fermentors.

Following expression in the host cell, the expressed product such as the polypeptide of interest can then be recovered from the culture of host cells. In order to obtain a maximum yield of the expressed product the cells are usually harvested at the end of the culture and lysed, such as lysing by lysozyme treatment, sonication or French Press. Thus, the polypeptides are usually first obtained as crude lysate of the host cells. They can then be purified by standard protein purification procedures known in the art which may include differential precipitation, molecular sieve chromatography, ion-exchange chromatography, isoelectric focusing, gel electrophoresis, affinity, and immunoaffinity chromatography. These well known and routinely practiced methods are described in, e.g., Ausubel et al., supra., and Wu et al. (eds.), Academic Press Inc., N.Y.; Immunochemical Methods In Cell And Molecular Biology, 1988.

FIGS. 1A-E show maps of plasmids expressing T7 lysozyme or variants thereof from an L-rhamnose inducible promoter. A, pTACO1-Lys comprises a cloDF13 origin of replication and a spectinomycin resistance marker; B, pTACO1-LysY comprises a cloDF13 origin of replication and a spectinomycin resistance marker and codes for the mutant LysY; C, pTACO2-Lys comprises a P15A origin of replication and a chloramphenicol resistance marker; D, pLEMO comprises a P15A origin of replication and a chloramphenicol resistance marker and codes for the mutant LysY; and E, pTACO3-LysY comprises a pSC101 derived repA origin of replication and a spectinomycin resistance marker and codes for the mutant LysY. The plasmids of FIG. 1A-E also include the two L-rhamnose-specific activators RhaS and RhaR. Sequences of the plasmids are given in the sequence listing at the end of the description.

FIG. 2 shows a model of the control of T7 RNA polymerase activity by titration of T7 lysozyme expression. T7 lysozyme expression is under the control of the rhaBAD promoter and is induced by the addition of L-rhamnose. In this case the amidase activity deficient T7 lysozyme mutant LysY is used.

Figure 3:
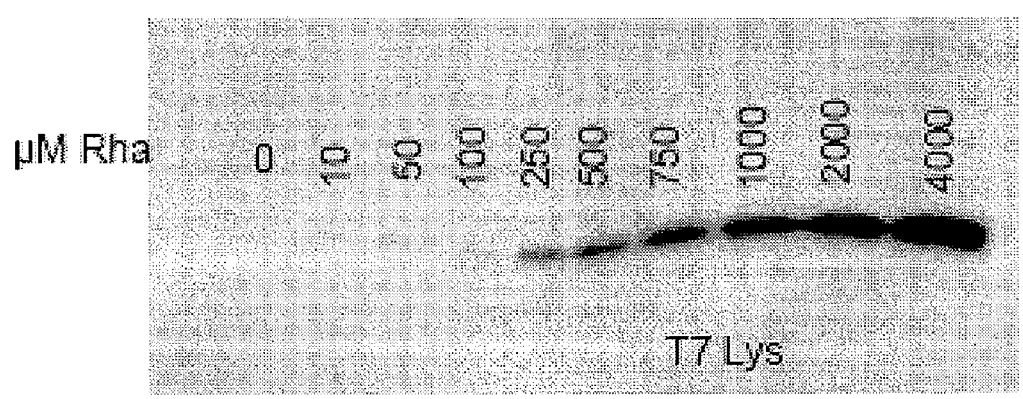
FIG. 3 shows expression levels of T7 lysozyme in Lemo21 (DE3) cells of the present invention, cultured in the presence of different concentrations of L-rhamnose.

FIG. 3 shows expression levels of T7 lysozyme in Lemo21 (DE3) cells cultured in the presence of different concentrations of L-rhamnose. T7 lysozyme expression was monitored by SDS-PAGE/western-blotting using an antibody against T7 lysozyme. Equal amounts—based on $OD_{600}$ readings—of whole-cell material were loaded per lane. The results show that the expression level of T7 lysozyme increases with increasing concentrations of L-rhamnose in the culture medium.

Figure 4:
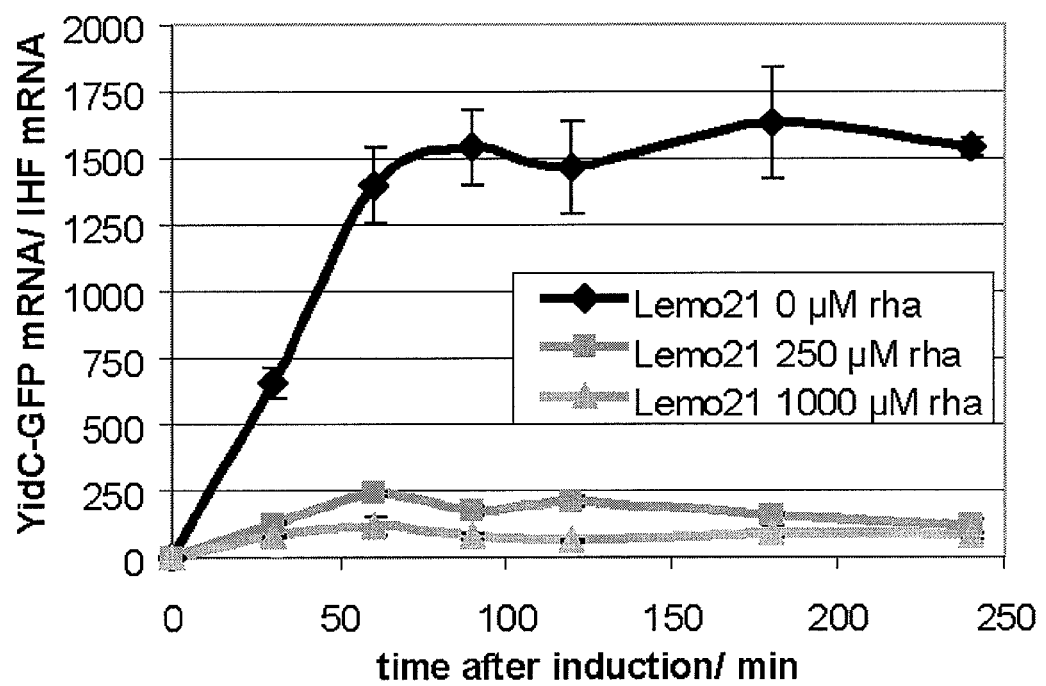
FIG. 4 shows mRNA levels of the recombinant protein YidC-GFP, expressed in Lemo21 (DE3) cells of the present invention, grown in the presence of different concentrations of L-rhamnose.

FIG. 4 shows mRNA levels of the recombinant protein YidC-GFP, expressed in Lemo21 (DE3) (BL21 (DE3) harboring pLemo) grown in the presence of different concentrations of L-rhamnose (here, rha). The figure shows a decreasing yield of mRNA, indicating a lower rate of transcription, with increasing concentrations of L-rhamnose. This further indicates an increased inhibition of T7 RNA polymerase by the increasing levels of T7 lysozyme achieved by the increasing levels of L-rhamnose.

Figure 5:
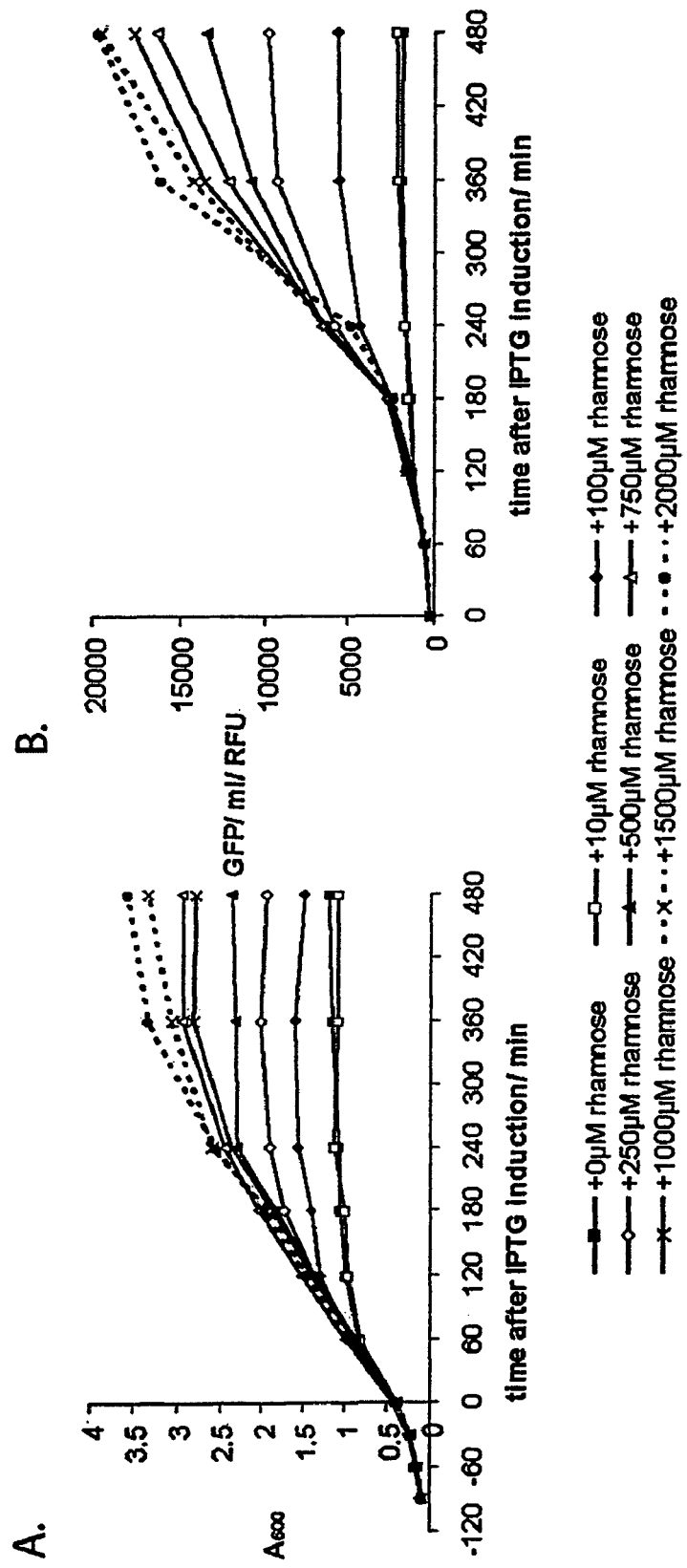
FIG. 5 shows A, growth and B, protein expression of Lemo21 (DE3) cells of the present invention, expressing the recombinant protein YidC-GFP and grown in the presence of different concentrations of L-rhamnose.

FIG. 5 shows A, growth and B, protein expression of Lemo21 (DE3) expressing the recombinant membrane protein YidC-GFP and grown in the presence of different concentrations of L-rhamnose. YidC-GFP expression was monitored by whole cell GFP fluorescence. The results of figure A shows an increasing level of growth with increasing levels of L-rhamnose (i.e. levels of T7 lysozyme), indicating that a lower rate of membrane protein expression, due to inhibition of T7 RNA polymerase, has a positive effect on cell viability and growth. The results of figure B indicate an increasing level of membrane protein expression and insertion into the membrane with increasing levels of L-rhamnose, i.e. with increasing levels of T7 lysozyme and decreasing rate of transcription.

Figure 6:
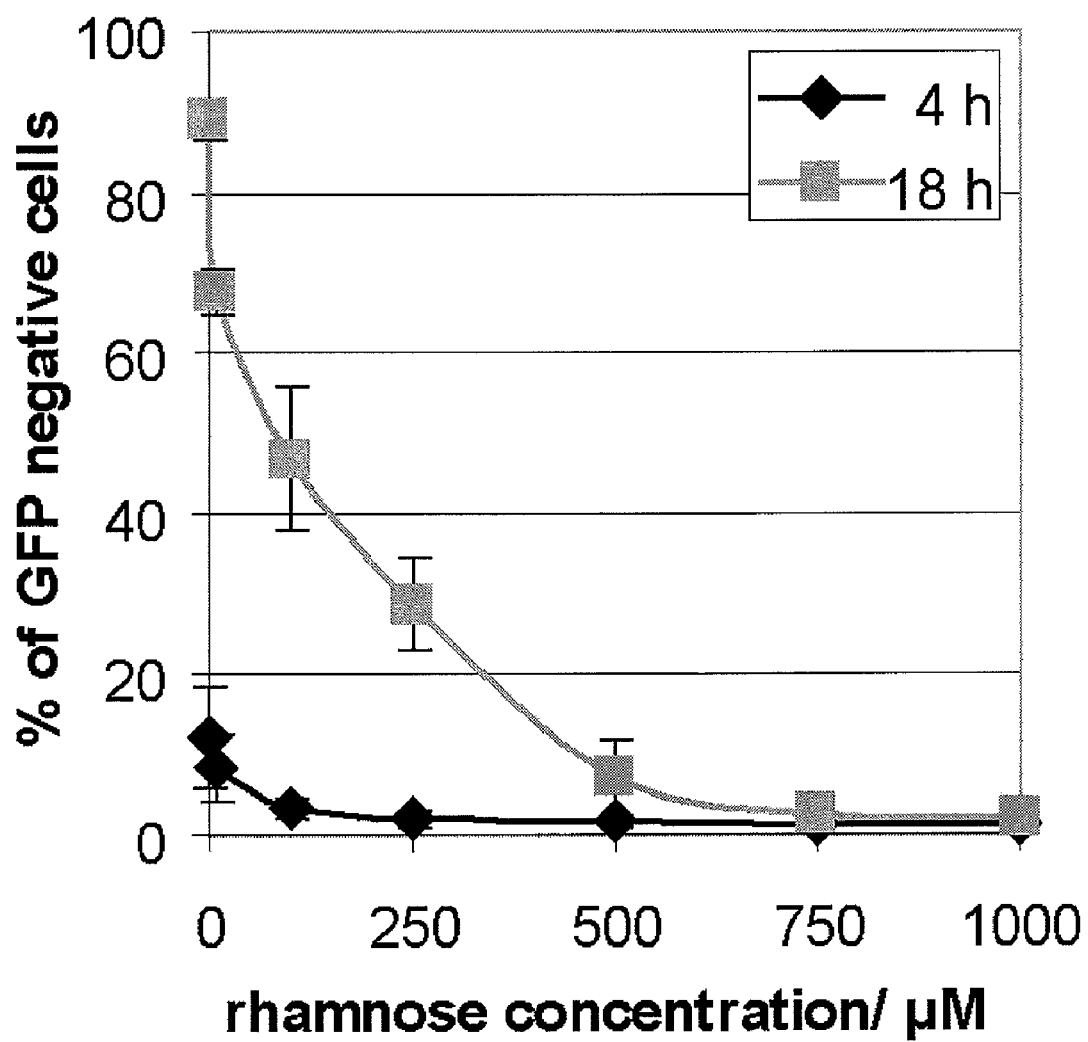
FIG. 6 shows the fraction of Lemo21 (DE3) cells not expressing YidC-GFP 4 hours and 18 hours, respectively, after induction with IPTG, in the presence of different concentrations of L-rhamnose.

FIG. 6 shows the fraction of cells not expressing YidC-GFP 4 hours and 18 hours, respectively, after induction with IPTG, in the presence of different concentrations of L-rhamnose. The results show that, most evidently after 18 hours, the fraction of YidC-GFP negative cells decreases with increasing levels of L-rhamnose (i.e. levels of T7 lysozyme), indicating that increasing L-rhamnose concentrations prevent overgrowth of non-expressing cells in the culture.

Figure 7:
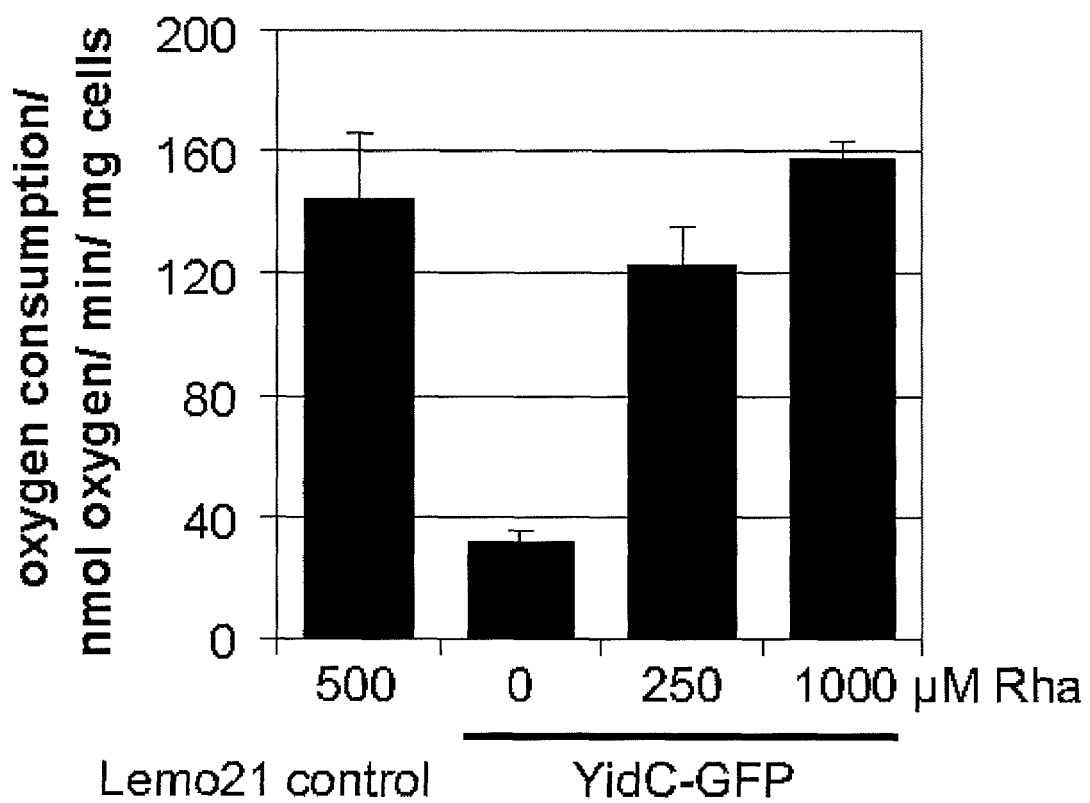
FIG. 7 shows the oxygen consumption of Lemo21 (DE3) cells of the present invention expressing the recombinant protein YidC-GFP, 4 hours after induction with IPTG grown in the presence of different concentrations of L-rhamnose.

FIG. 7 shows the oxygen consumption of Lemo21 (DE3) expressing the recombinant protein YidC-GFP 4 hours after induction with IPTG grown in the presence of different concentrations of L-rhamnose. The results indicate that, compared to control cells (not expressing membrane proteins), the respiration of cells having full T7 RNA polymerase activity (no presence of L-rhamnose and thus no T7 lysozyme inhibition) is affected, whereas the respiration of cells in the presence of an optimally set concentration of L-rhamnose (and thus optimal, down regulated T7RNA polymerase activity) is not affected.

Figure 8:
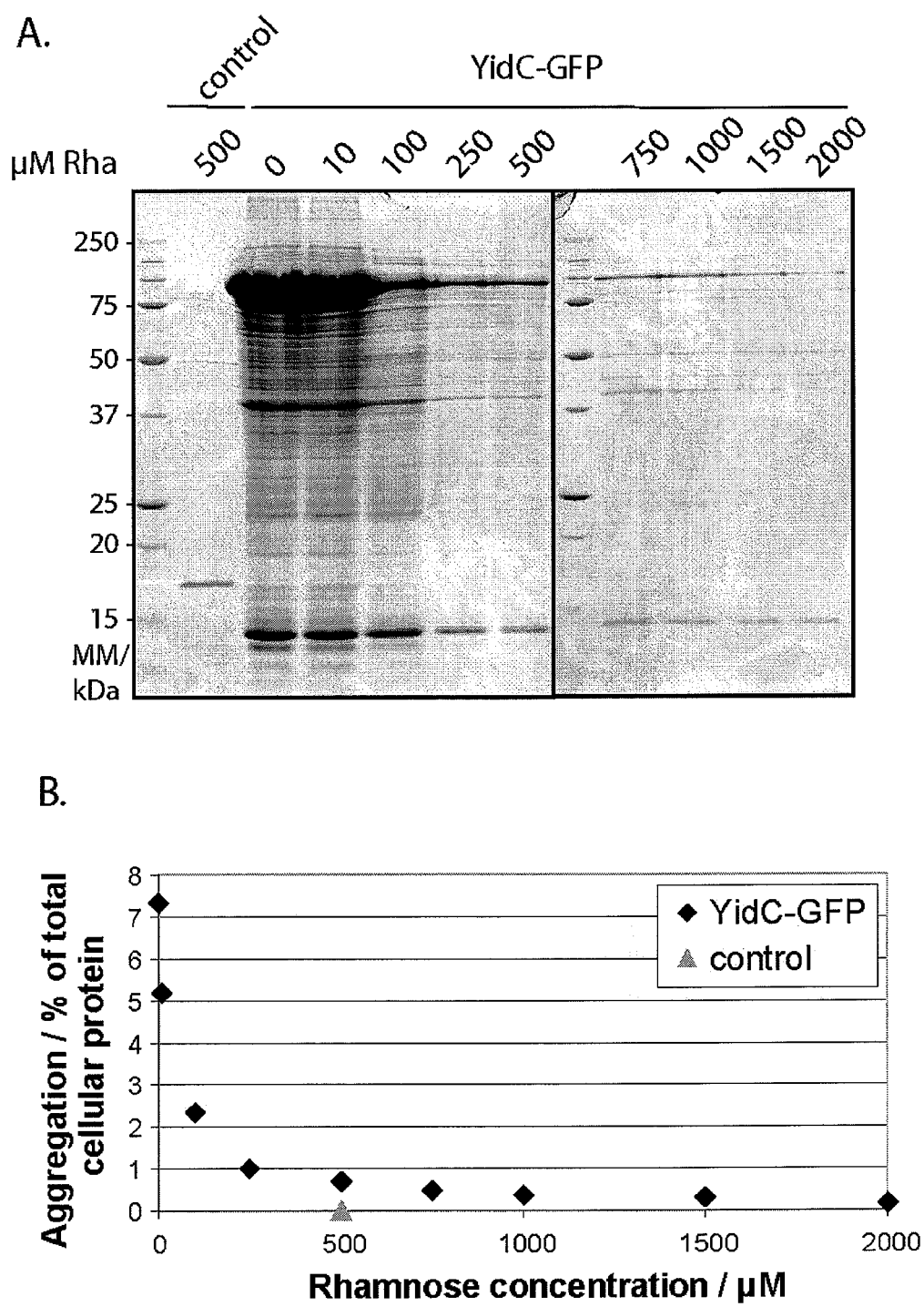
FIG. 8 shows the aggregation of proteins in the cytoplasm of Lemo21 (DE3) cells of the present invention, expressing the recombinant protein YidC-GFP for 4 hours, in the presence of different concentrations of L-rhamnose.

FIG. 8 shows the aggregation of proteins in Lemo21 (DE3) expressing the recombinant protein YidC-GFP for 4 hours, in the presence of different concentrations of L-rhamnose. A, protein aggregates were isolated and analyzed by SDS- PAGE. Gels were stained by colloidal Coomassie. B, quantification of the fraction of aggregated proteins in Lemo21 (DE3) upon overexpression of YidC-GFP. The results show decreasing levels of cytoplasmic protein aggregates with increasing levels of L-rhamnose, indicating that the down regulated activity of T7 RNA polymerase, via increasing levels of T7 lysozyme, leads to decreasing levels of protein aggregation.

Figure 9:
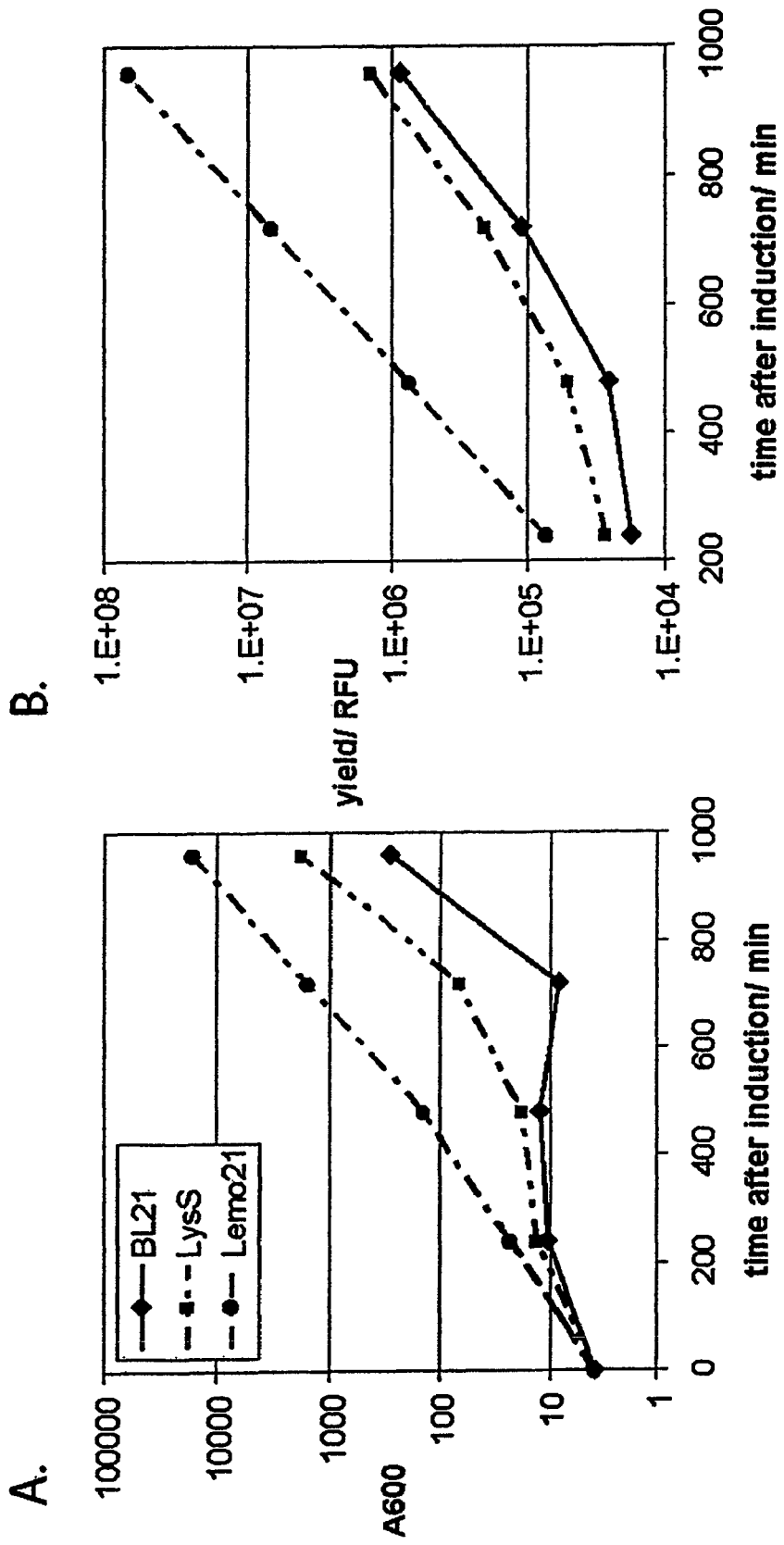
FIG. 9 shows A, growth and B, protein expression of the recombinant protein YidC-GFP in a semi-continuous culture, in a comparison between different strains.

FIG. 9 shows A, growth and B, protein expression of the recombinant protein YidC-GFP in a semi-continuous culture, in a comparison between different strains (BL21 (DE3), BL21 (DE3)pLysS and Lemo21 (DE3)). Strains overexpressing YidC-GFP fusions were back-diluted 1:10 every 4 hours in medium with IPTG. Lemo21 (DE3) was grown in the presence of an optimally set concentration (1000 µM) of L-rhamnose. Growth and protein expression were monitored by measuring the A600 and whole cell GFP fluorescence, respectively. The graphs show accumulated values. The results show that Lemo21 (DE3) expressing YidC-GFP is completely stable and performs as well as or better than the other strains.

Figure 10:
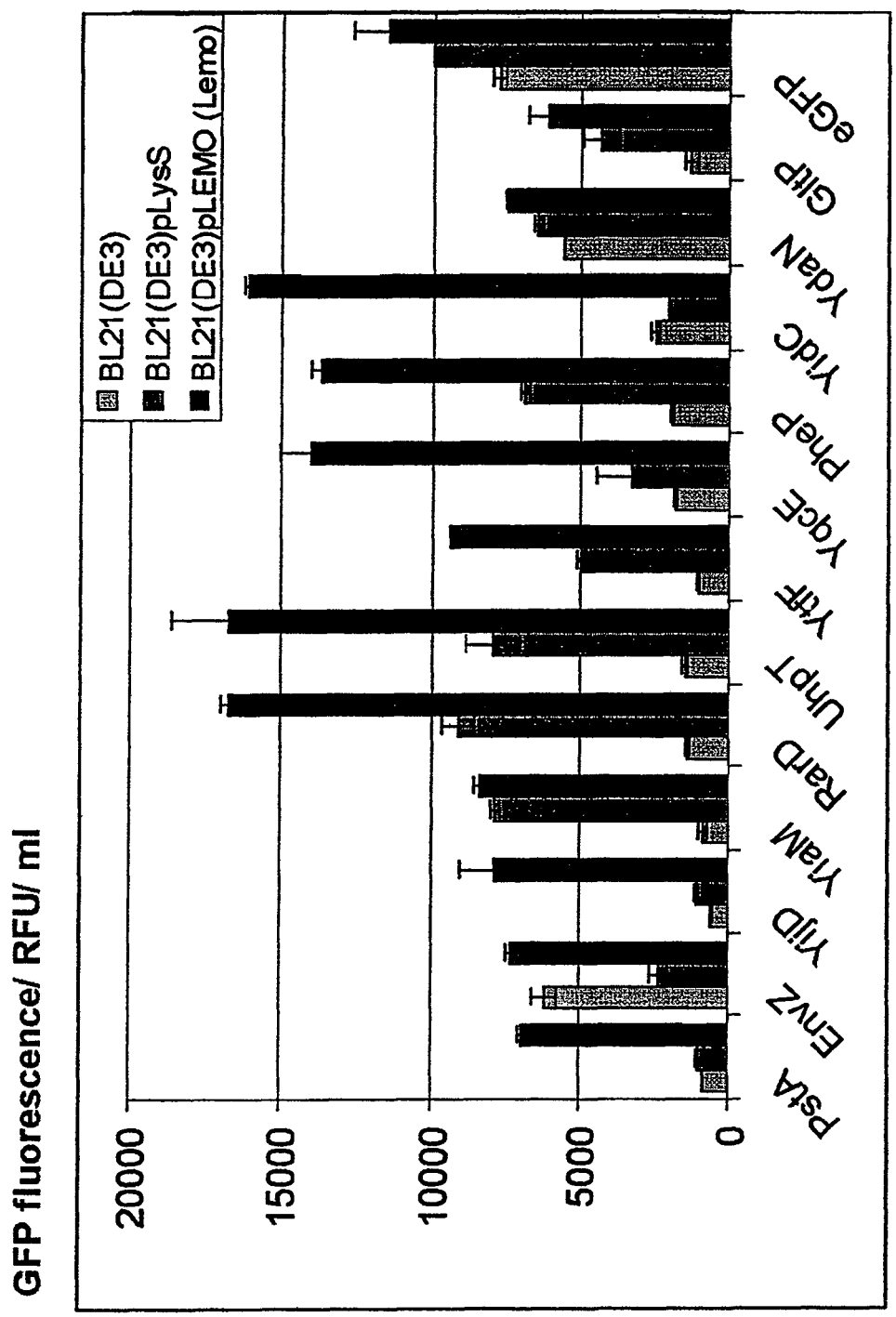
FIGS. 10A and 10B show expression of GFP-fusion membrane proteins in Lemo21 (DE3) cells of the present invention, compared to the expression in other $E.$ $coli$ strains.
Figure 10:
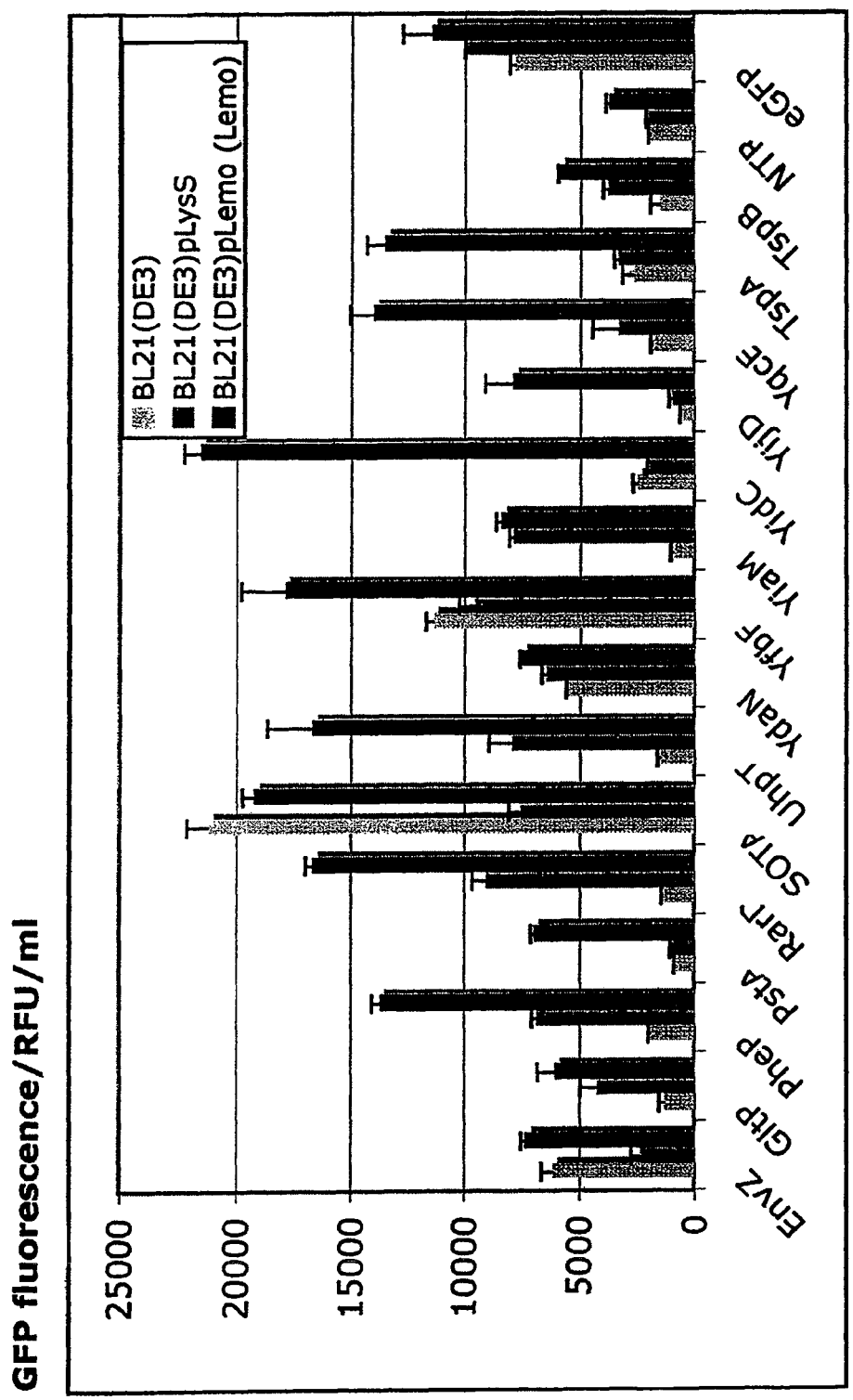

FIGS. 10A and 10B show a comparison of expression (GFP fluorescence) of GFP-fusion proteins in the different strains BL21(DE3), BL21(DE3)pLysS and Lemo21(DE3). The proteins include $E.$ $coli$ membrane proteins EnvZ, G1tP, PheP, PstA, RarD, UhpT, YfbF, YiaM, YidC, YijD, YqcE, YdaN; $Shewanella$ $oneidensis$ membrane proteins transporter A (SOTA); rat membrane protein neurotensin receptor (NTR); the human membrane proteins tetraspannin TspA and TspB; and the soluble protein eGFP. Optimal L-rhamnose concentration was determined and used for each protein. The expression levels of eGFP are divided by 50 to fit them into the graph. Expression of the GFP fusion proteins and eGFP was monitored by whole cell GFP fluorescence. The $E.$ $coli$ osmolarity sensor protein EnvZ and the $S.$ $oneidensis$ transporter A (SOTA) only expressed well in BL21(DE3) and Lemo(DE3) without any L-rhamnose. In most cases Lemo21 (DE3) outperformed BL21(DE3) and BL21(DE3)pLysS, indicating that Lemo21(DE3) allows for optimization of overexpression of membrane proteins by using only one strain and a simple L-rhamnose titration rather than a multitude of strains.

Figure 11:
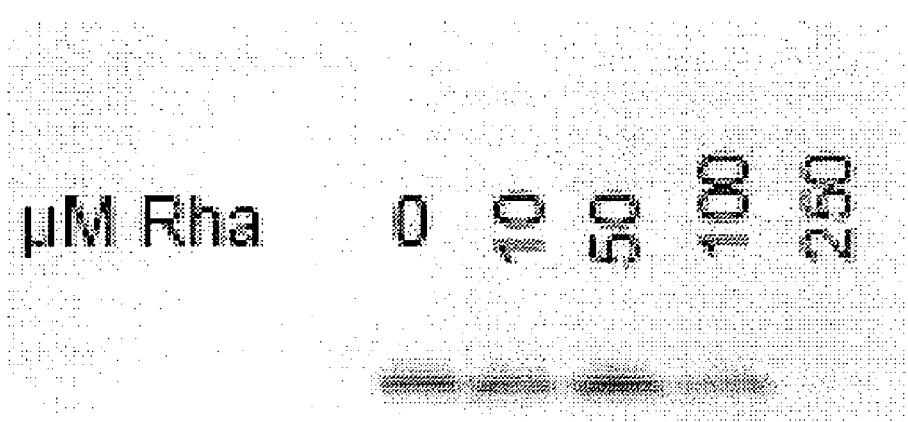
FIG. 11 shows expression levels of the soluble, chaperone requiring luciferase-His$_8$ in Lemo21 (DE3) cells of the present invention cultured in the presence of different concentrations of L-rhamnose.

FIG. 11 shows expression levels of the soluble, chaperone requiring luciferase-His$_8$, luciferase tagged with a C-terminal His$_8$ tag, in Lemo21-(DE3) cells cultured in the presence of different concentrations of L-rhamnose. Luciferase-His$_8$ expression was monitored by SDS-PAGE/Western-blotting using an antibody against His-tags. Equal amounts—based on OD$_{600}$ readings—of whole-cell material were loaded per lane. In this case optimal concentration for achieving the highest expression levels is 50 µM of L-rhamnose. The results show that the expression system of the present invention is suitable and allows for optimization of overexpression also of soluble, chaperone requiring proteins.

Figure 12:
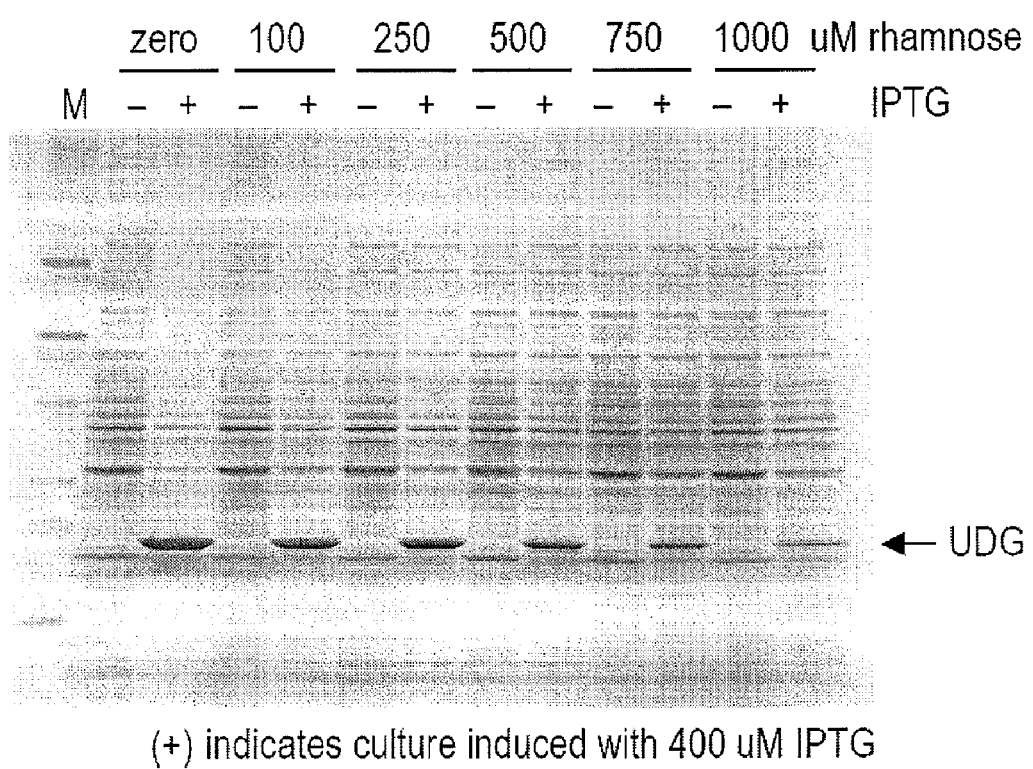
FIG. 12 shows A, expression levels of $E.$ $coli$ uracil DNA glycosylase, a soluble cytoplasmic protein, expression in Lemo21(DE3) cells cultured in the presence of different concentrations of L-rhamnose, and B, expression levels of $E.$ $coli$ uracil DNA glycosylase in Lemo21(DE3) cells in the absence of rhamnose in comparison with expression in other $E.$ $coli$ strains.
Figure 12:
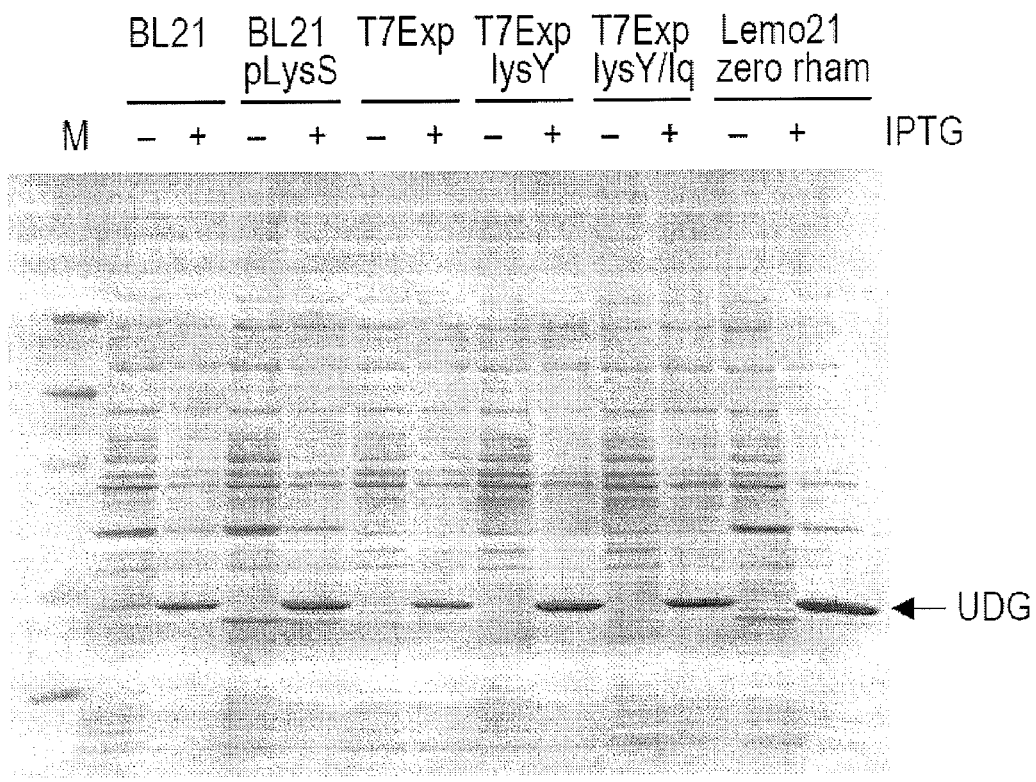

FIG. 12 shows A, expression levels of $E.$ $coli$ uracil DNA glycosylase, a soluble cytoplasmic protein, expression in Lemo21 (DE3) cells cultured in the presence of different concentrations of L-rhamnose. Equal amounts of cells were loaded per lane of an SDS-PAGE gel and the gel was upon completion of the run stained with Coomassie, and B, $E.$ $coli$ uracil DNA glycosylase expression in Lemo21 (DE3) cells cultured in the presence of 0 µM L-rhamnose, compared to $E.$ $coli$ uracil DNA glycosylase expression in $E.$ $coli$ BL21 (DE3), BL21 (DE)+pLysS, T7 Express, T7 Express+pLysY and T7 Express+pLysY/Iq. The results of FIG. 12A is another example showing that the expression system of the present invention is suitable for soluble proteins. The expression is better in Lemo21 (DE3) compared to the other strains even though no rhamnose was added. The effect is likely due to background expression of T7Lys.

EXAMPLES

All experiments may be performed by following the description, and with reference to standard handbooks known in the field, such as Maniatis et al.(Sambrook, J., Fritsch, E.F., and Maniatis, T., in Molecular Cloning: A Laboratory Manual. Cold Spring Harbor Laboratory Press, NY, Vol. 1, 2, 3 (1989) or methods available at the Cold Spring Harbor Protocols website.)

Materials that were used: Amplification of DNA was performed using Roche Expand Long Template PCR System. Extraction of DNA from agarose gels was done with Qiaex II from Qiagen. Purification of products from enzymatic reactions was done with the QIAquick PCR Purification Kit from Qiagen. Restriction enzymes were from Fermentas. T4 ligase was from Invitrogen. Quikchange site directed mutagenesis kit was from Stratagene. dNTPs were from Fermentas. Sequencing was done using BigDye Terminator v1.1 cycle sequencing kit from Applied biosystems.

Construction of vectors containing T7 lysozyme or variants thereof under the control of the rhaBAD promoter.

Example 1

Construction of pTACO1 and pTACO2: A portion of pRhaI09 (Giacalone, et al. (2006) Biotechniques 40:355-64) containing the genes rhaS, rhaR, the promoter rhaBAD and the multiple cloning site was PCR amplified using primers 'pRha_EheI_f, GCGCGCGGCGCCCGATAAGCTTAAT-TAATCTTTCTGCG' (SEQ ID NO: 7) and 'pRha_XmaJI_r, CGCGCGCCTAGGGCATATGAATACGC-CCTTTCGGATG' (SEQ ID NO: 8). The PCR product was run on an 1% agarose gel and purified using Qiaex II from Qiagen. The purified PCR product was digested with EheI and XmaJI and ligated into the backbone of pACYC-DUET-1 and pCDF-DUET-1, respectively, (Novagene) (Tolia and Joshua-Tor (2006) Nat Methods 3:55-64) digested with EheI and XmaJI. The XbaI restriction site within the p15A origin of pACYC-DUET-1 was eliminated by Quikchange site directed mutagenesis (TCTAGA to TCTAGG) following the instructions of the manufacturer (Stratagene). The plasmid resulting from ligation of the said PCR product with pCDF-DUET-1 was named pTACO1, the plasmid resulting from ligation of the said PCR product with pACYC-DUET-1 was named pTACO2.

Example 2

Construction of pTACO1-Lys, pTACO1-LysY, pTACO2-Lys, and pLEMO pTACO1-Lys, pTACO1-LysY, pTACO2-Lys, and pLemo were constructed by ligating the PCR-amplified product of T7 Lysozyme or the T7 Lysozyme mutant K128Y (Cheng, et al. (1994) Proc Natl Acad Sci U S A 91:4034-8) (LysY) into pTACO1 and pTACO2, respectively, digested with SalI and BamHI. PCR primers used were 'T7Lys_SalI_f, GCGCGCGTCGACATGGCTCGTGTA-CAGTTTAA' (SEQ ID NO: 9) and 'T7Lys_BamHI_r, CGCGCGGGATCCTTATCCACGGTCAGAAGTGA' (SEQ ID NO: 10).

Example 3

Construction of pTACO3-LysY

A portion of pCL1920 (Lerner and Inouye (1990) Nucleic Acids Res 18:4631) containing the gene aadA1 and the pSC101 origin of replication repA was PCR amplified using primers 'pCL1920_XmaJI_f, CGCGCGCCTAGGGACAGTAAGACGGGTAAGCC' (SEQ ID NO: 11) and 'pCL1920_HindIII_r, GCGCGCAAGCTTCTAACGCTTGAGTTAAGCCG' (SEQ ID NO: 12). The purified PCR product was digested and cloned into the fragment of pTACO1-LysY digested with HindIII and XmaJI that contained the genes rhaS, rhaR, the promoter rhaBAD and the gene LysY. The resulting plasmid was called pTACO3-LysY.

The nucleotide sequences of the plasmids were confirmed by sequencing (BM Labbet A B, Furusund, Sweden).

Example 4

Construction of Host Cells Carrying pLemo

*E. coli* BL21 (DE3) cells were used as host cells. BL21 (DE3) is well known and commercially available a strain carrying DE3, a λ prophage comprising the T7 RNA polymerase gene and lacIq. The gene encoding the T7 RNA polymerase is under control of the lacUV5 promoter. Chemical or electrocompetent BL21 (DE3) cells were transformed with pLemo using standard procedures, resulting in Lemo21 (DE3), i.e. BL21 (DE3) cells harboring pLEMO.

Example 5

Expression of target protein and titration of T7RNAP activity by expression of T7 lysozyme: Cells of the respectively stated strains were transformed with a pET28 (a+) derived expression vector—comprising the gene encoding the target protein, under control of a T7 promotor. Membrane target proteins were C-terminally fused to GFP, while the soluble target proteins luciferase-His$_8$ and *E. coli* uracil DNA glycosylase were not fused to GFP. Cells were grown aerobically in standard Luria-Bertani broth supplemented with kanamycin (50 μg/ml) (and chloramphenicol (30 μg/ml) if expression strain contained a pACYC derived plasmid). Over night cultures were diluted 1:50. Growth was monitored by measuring the OD$_{600}$ with a Shimadzu UV-1601 spectrophotometer. T7 lysozyme expression was induced by addition of 10-4000 μM L-rhamnose to the culture medium already at the start. T7 lysozyme expression was monitored using SDS-PAGE/Western-blotting. For all experiments, target protein expression was induced by the addition of 0.4 mM isopropyl-β-D-thiogalactopyranoside (IPTG) (final concentration) at an OD$_{600}$ of 0.4-0.5 and cells were harvested at various timepoints after induction for further analysis. Expression of the target protein was monitored by measuring GFP fluorescence as described before (Drew, D., et al. (2005) Protein Sci 14:2011-7; Drew, D., et al. (2006) Nat Methods, 2006. 3:303-13). GFP fluorescence is a good indicator for membrane protein expression as only in the membrane inserted membrane proteins are fluorescent (Drew, D. E., et al. (2001) FEBS Letters 507:220-4). Analysis of cells overexpressing GFP fusion proteins and control cells by means of flow cytometry was done as described before using a FACSCalibur (BD Biosciences) instrument (Wagner, et al. (2007) Mol Cell Proteomics 6:1527-50). Expression of luciferase-His$_8$ and *E. coli* uracil DNA glycosylase were monitored using SDS-PAGE/Western-blotting and SDS-PAGE/Coomassie staining, respectively.

The invention claimed is:

1. A host cell capable of expressing T7 RNA polymerase, the host cell comprising a first nucleic acid having a T7 lysozyme gene or a T7 lysozyme variant gene and a tunable promoter for controlling the expression of the T7 lysozyme gene or the T7 lysozyme variant gene.

2. The host cell of claim 1 further comprising a second nucleic acid having a T7 promoter operably linked to a nucleic acid sequence encoding a target polypeptide, whereby expression of the target polypeptide is tuned via controlling the expression of the T7 lysozyme gene or the T7 lysozyme variant gene.

3. The host cell of claim 2, wherein said first nucleic acid comprising the tunable promoter is a first vector and said second nucleic acid comprising the T7 promoter is a second vector and wherein the first and the second vectors are compatible.

4. The host cell of claim 1, wherein said tunable promoter is tunable by rhamnose or arabinose.

5. The host cell of claim 1, wherein said tunable promoter is tunable by light.

6. The host cell of claim 1, wherein said tunable promoter is tunable by temperature.

7. The host cell of claim 1, wherein said first nucleic acid comprises a selection marker.

8. The host cell of claim 7, wherein the selection marker is an antibiotic selection marker.

9. The host cell of claim 1, wherein the T7 lysozyme variant gene encodes LysY.

10. The host cell of claim 1, wherein said first nucleic acid is at least 80% identical to a nucleic acid chosen from the group comprising SEQ ID NOS: 1-5.

11. The host cell of claim 10, wherein said first nucleic acid is substantially identical to a nucleic acid chosen from the group comprising SEQ ID NOS: 1-5.

12. A host cell of claim 1, selected from the group of *E. coli*, *Pseudomonas aeruginosa*, *Erwinia carotovora*, *Salmonella choleraesuis*, *Agrobacterium tumefaciens*, *Chromobacterium violaceum*, *Lactococcus lactis*, *Bacillus subtilis*, *Salmonella*, *Saccharomyces cerevisiae*, *Pichia pastoris*, *Kluyveromyces lactis*, CHO, NSO, HEK293, HeLa, Sf9, tobacco, rice and *Leishmania tarentolae*.

13. A method for producing a target polypeptide, comprising the steps of;
   a) providing a host cell according to claim 2;
   b) inducing expression of the target polypeptide;
   c) controlling the expression of the target polypeptide by tuning of said tunable promoter and thereby of the expression of said T7 lysozyme; and optionally
   d) isolating the polypeptide.

14. The method of claim 13, wherein the induction of expression of the target polypeptide is performed by inducing the expression of a T7 RNA polymerase gene, or a variant thereof.

15. The method of claim 13, wherein the tuning of the tunable promoter, or a variant thereof, is accomplished by any of: light induction, temperature adjustment, and addition of a chemical inducer.

16. A nucleic acid comprising a T7 lysozyme gene or a T7 lysozyme variant gene and a tunable rhaBAD promoter for controlling the expression of the T7 lysozyme gene or the T7 lysozyme variant gene.

17. A nucleic acid according to claim 16 which is at least 80% identical to a nucleic acid chosen from the group SEQ ID NOS: 1-5.

18. A nucleic acid according to claim 17 chosen from the group SEQ ID NOS: 1-5.

19. A method of controlling the expression of a target polypeptide via T7 lysozyme comprising transforming a host cell capable of expressing T7 RNA polymerase with the nucleic acid of claim 16.

20. The method of claim 15, wherein the chemical inducer is rhamnose or arabinose.

* * * * *

SEQUENCE LISTING

```
<160> NUMBER OF SEQ ID NOS: 17

<210> SEQ ID NO 1
<211> LENGTH: 5001
<212> TYPE: DNA
<213> ORGANISM: Artificial
<220> FEATURE:
<223> OTHER INFORMATION: pLemo plasmid

<400> SEQUENCE: 1
gcccattttc ctgtcagtaa cgagaaggtc gcgaattcag gcgcttttta gactggtcgt       60
aatgaaattc aggaggtggt cgacatggct cgtgtacagt ttaaacaacg tgaatctact      120
gacgcaatct ttgttcactg ctcggctacc aagccaagtc agaatgttgg tgtccgtgag      180
attcgccagt ggcacaaaga gcagggttgg ctcgatgtgg gataccactt tatcatcaag      240
cgagacggta ctgtggaggc aggacgagat gagatggctg taggctctca cgctaagggt      300
tacaaccaca actctatcgg cgtctgcctt gttggtggta tcgacgataa aggtaagttc      360
gacgctaact ttacgccagc ccaaatgcaa tcccttcgct cactgcttgt cacactgctg      420
gctaagtacg aaggcgctgt gcttcgcgcc catcatgagg tggcgccgta cgcttgccct      480
tcgttcgacc ttaagcgttg gtgggagaag aacgaactgg tcacttctga ccgtggataa      540
ggatccccgc gccctcatcc gaaagggcgt attcatatgc cctaggctgc tgccaccgct      600
gagcaataac tagcataacc ccttgggcc tctaaacggg tcttgagggg ttttttgctg      660
aaacctcagg catttgagaa gcacacggtc acactgcttc cggtagtcaa taaaccggta      720
aaccagcaat agacataagc ggctatttaa cgaccctgcc ctgaaccgac gaccgggtcg      780
```

```
aatttgctttt cgaatttctg ccattcatcc gcttattatc acttattcag gcgtagcacc      840
aggcgtttaa gggcaccaat aactgcctta aaaaaattac gccccgccct gccactcatc      900
gcagtactgt tgtaattcat taagcattct gccgacatgg aagccatcac aaacggcatg      960
atgaacctga atcgccagcg gcatcagcac cttgtcgcct tgcgtataat atttgcccat     1020
agtgaaaacg ggggcgaaga agttgtccat attggccacg tttaaatcaa aactggtgaa     1080
actcacccag ggattggctg agacgaaaaa catattctca ataaacc ctt tagggaaata    1140 ggccaggttt tcaccgtaac acgccacatc ttgcgaatat atgtgtagaa actgccggaa     1200
atcgtcgtgg tattcactcc agagcgatga aaacgtttca gtttgctcat ggaaaacggt     1260
gtaacaaggg tgaacactat cccatatcac cagctcaccg tctttcattg ccatacggaa     1320
ctccggatga gcattcatca ggcgggcaag aatgtgaata aaggccggat aaaacttgtg     1380 cttattttc tttacggtct ttaaaaaggc cgtaatatcc agctgaacgg tctggttata     1440
ggtacattga gcaactgact gaaatgcctc aaaatgttct ttacgatgcc attgggatat     1500
atcaacggtg gtatatccag tgatttttt ctccatttta gcttccttag ctcctgaaaa     1560
tctcgataac tcaaaaaata cgcccggtag tgatcttatt tcattatggt gaaagttgga     1620
acctcttacg tgccgatcaa cgtctcattt cgccaaaag ttgcccagg gcttcccggt       1680 atcaacaggg acaccaggat ttatttattc tgcgaagtga tcttccgtca caggtattta     1740
ttcggcgcaa agtgcgtcgg gtgatgctgc caacttactg atttagtgta tgatggtgtt     1800
tttgaggtgc tccagtggct tctgtttcta tcagctgtcc ctcctgttca gctactgacg     1860
gggtggtgcg taacggcaaa agcaccgccg gacatcagcg ctagcggagt gtatactggc     1920
ttactatgtt ggcactgatg agggtgtcag tgaagtgctt catgtggcag gagaaaaaag     1980
gctgcaccgg tgcgtcagca gaatatgtga tacaggatat attccgcttc ctcgctcact     2040
gactcgctac gctcggtcgt tcgactgcgg cgagcgaaa tggcttacga acggggcgga     2100
gatttcctgg aagatgccag gaagatactt aacaggaag tgagagggcc gcggcaaagc     2160 cgttttttcca taggctccgc ccccctgaca agcatcacga atctgacgc tcaaatcagt     2220 ggtggcgaaa cccgacagga ctataaagat accaggcgtt tccc ctggcg ctccctcgt     2280 gcgctctcct gttcctgcct ttcggtttac cggtgtcatt ccgctgttat ggccgcgttt     2340
gtctcattcc acgcctgaca ctcagttccg ggtaggcagt tcgctccaag ctggactgta     2400
tgcacgaacc ccccgttcag tccgaccgct gcgccttatc cggtaactat cgtcttgagt     2460
ccaacccgga aagacatgca aaagcaccac tggcagcagc cactggtaat tgatttagag     2520
gagttagtct tgaagtcatg cgccggttaa ggctaaactg aaaggacaag ttttggtgac     2580
tgcgctcctc caagccagtt acctcggttc aaagagttgg tagctcagag aaccttcgaa     2640
aaaccgccct gcaaggcggt tttttcgttt tcagagcaag agattacgcg cagaccaaaa     2700
cgatctcaag aagatcatct tattaatcag ataaaatatt tctaggtttc agtgcaattt     2760
atctcttcaa atgtagcacc tgaagtcagc cccatacgat ataagttgta attctcatgt     2820
tagtcatgcc ccgcgcccac cggaaggagc tgactgggtt gaaggctctc aagggcatcg     2880
gtcgagatcc cggtgcctaa tgagtgagct aacttacatt aattgcgttg cgctcactgc     2940
ccgctttcca gtcgggaaac ctgtcgtgcc agctgcatta atgaatcggc caacgcgcgg     3000
ggagaggcgg tttgcgtatt gggcgcccga taagcttaat taatctttct gcgaattgag     3060
atgacgccac tggctgggcg tcatcccggt ttcccgggta acaccaccg aaaaatagtt      3120 actatcttca aagccacatt cggtcgaaat atcactgatt aacaggcggc tatgctggag     3180
```

```
aagatattgc gcatgacaca ctctgacctg tcgcagatat tgattgatgg tcattccagt    3240
ctgctggcga aattgctgac gcaaaacgcg ctcactgcac gatgcctcat cacaaaattt    3300
atccagcgca aagggacttt tcaggctagc cgccagccgg gtaatcagct tatccagcaa    3360
cgtttcgctg gatgttggcg gcaacgaatc actggtgtaa cgatggcgat tcagcaacat    3420
caccaactgc ccgaacagca actcagccat ttcgttagca aacggcacat gctgactact    3480
ttcatgctca agctgaccga taacctgccg cgcctgcgcc atccccatgc tacctaagcg    3540
ccagtgtggt tgccctgcgc tggcgttaaa tcccggaatc gccccctgcc agtcaagatt    3600
cagcttcaga cgctccgggc aataaataat attctgcaaa accagatcgt taacggaagc    3660
gtaggagtgt ttatcgtcag catgaatgta aaagagatcg ccacgggtaa tgcgataagg    3720
gcgatcgttg agtacatgca ggccattacc gcgccagaca atcaccagct cacaaaaatc    3780
atgtgtatgt tcagcaaaga catcttgcgg ataacggtca gccacagcga ctgcctgctg    3840
gtcgctggca aaaaatcat cttttgagaag ttttaactga tgcgccaccg tggctacctc    3900
ggccagagaa cgaagttgat tattcgcaat atggcgtaca aatacgttga aagattcgc    3960 gttattgcag aaagccatcc cgtccctggc gaatatcacg cggtgaccag ttaaactctc    4020
ggcgaaaaag cgtcgaaaag tggttactgt cgctgaatcc acagcgatag gcgatgtcag    4080
taacgctggc ctcgctgtgg cgtagcagat gtcgggcttt catcagtcgc aggcggttca    4140
ggtatcgctg aggcgtcagt cccgtttgct gcttaagctg ccgatgtagc gtacgcagtg    4200
aaagagaaaa ttgatccgcc acggcatccc aattcacctc atcggcaaaa tggtcctcca    4260
gccaggccag aagcaagttg agacgtgatg cgctgttttc caggttctcc tgcaaactgc    4320
ttttacgcag caagagcagt aattgcataa caagatctc gcgactggcg gtcgagggta    4380 aatcatttc cccttcctgc tgttccatct gtgcaaccag ctgtcgcacc tgctgcaata    4440
cgctgtggtt aacgcgccag tgagacggat actgcccatc cagctcttgt ggcagcaact    4500
gattcagccc ggcgagaaac tgaaatcgat ccggcgagcg atacagcaca ttggtcagac    4560
acagattatc ggtatgttca tacagatgcc gatcatgatc gcgtacgaaa cagaccgtgc    4620
caccggtgat ggtataggc tgcccattaa acacatgaat acccgtgcca tgttcgacaa    4680
tcacaatttc atgaaaatca tgatgatgtt caggaaaatc cgcctgcggg agccggggtt    4740
ctatcgccac ggacgcgtta ccagacggaa aaaaatccac actatgtaat acggtcatac    4800
tggcctcctg atgtcgtcaa cacggcgaaa tagtaatcac gaggtcaggt tcttaccta    4860 aattttcgac ggaaaccac gtaaaaaacg tcgatttttc aagatacagc gtgaattttc    4920
aggaaatgcg gtgagcatca catcaccaca attcagcaaa ttgtgaacat catcacgttc    4980
atctttccct ggttgccaat g                                              5001

<210> SEQ ID NO 2
<211> LENGTH: 4774
<212> TYPE: DNA
<213> ORGANISM: Artificial
<220> FEATURE:
<223> OTHER INFORMATION: pTAC01-Lys plasmid

<400> SEQUENCE: 2
gcccattttc ctgtcagtaa cgagaaggtc gcgaattcag gcgcttttta gactggtcgt      60
aatgaaattc aggaggttgt cgacatggct cgtgtacagt ttaaacaacg tgaatctact     120
gacgcaatct ttgttcactg ctcggctacc aagccaagtc agaatgttgg tgtccgtgag     180
attcgccagt ggcacaaaga gcagggttgg ctcgatgtgg gataccactt tatcatcaag     240
```

```
cgagacggta ctgtggaggc aggacgagat gagatggctg taggctctca cgctaagggt        300
tacaaccaca actctatcgg cgtctgcctt gttggtggta tcgacgataa aggtaagttc        360
gacgctaact ttacgccagc ccaaatgcaa tcccttcgct cactgcttgt cacactgctg        420
gctaagtacg aaggcgctgt gcttcgcgcc catcatgagg tggcgccgaa agcttgccct        480
tcgttcgacc ttaagcgttg gtgggagaag aacgaactgg tcacttctga ccgtggataa        540
ggatccccgc gccctcatcc gaaagggcgt attcatatgc cctaggctgc tgccaccgct        600
gagcaataac tagcataacc ccttggggcc tctaaacggg tcttgagggg ttttttgctg        660
aaacctcagg catttgagaa gcacacggtc acactgcttc cggtagtcaa taaaccggta        720
aaccagcaat agacataagc ggctatttaa cgaccctgcc ctgaaccgac gaccgggtca        780
tcgtggccgg atcttgcggc ccctcggctt gaacgaattg ttagacatta tttgccgact        840
accttggtga tctcgccttt cacgtagtgg acaaattctt ccaactgatc tgcgcgcgag        900
gccaagcgat cttcttcttg tccaagataa gcctgtctag cttcaagtat gacgggctga        960
tactgggccg gcaggcgctc cattgcccag tcggcagcga catccttcgg cgcgattttg       1020
ccggttactg cgctgtacca aatgcgggac aacgtaagca ctacatttcg ctcatcgcca       1080
gcccagtcgg gcggcgagtt ccatagcgtt aaggtttcat ttagcgcctc aaatagatcc       1140
tgttcaggaa ccggatcaaa gagttcctcc gccgctggac ctaccaaggc aacgctatgt       1200
tctcttgctt ttgtcagcaa gatagccaga tcaatgtcga tcgtggctgg ctcgaagata       1260
cctgcaagaa tgtcattgcg ctgccattct ccaaattgca gttcgcgctt agctggataa       1320
cgccacggaa tgatgtcgtc gtgcacaaca atggtgactt ctacagcgcg gagaatctcg       1380
ctctctccag gggaagccga agtttccaaa aggtcgttga tcaaagctcg ccgcgttgtt       1440
tcatcaagcc ttacggtcac cgtaaccagc aaatcaatat cactgtgtgg cttcaggccg       1500
ccatccactg cggagccgta caaatgtacg ccagcaacg tcggttcgag atggcgctcg       1560
atgacgccaa ctacctctga tagttgagtc gatacttcgg cgatcaccgc ttccctcata       1620
ctcttccttt ttcaatatta ttgaagcatt tatcagggtt attgtctcat gagcggatac       1680
atatttgaat gtatttagaa aaataaacaa atagctagct cactcggtcg ctacgctccg       1740
ggcgtgagac tgcggcgggc gctgcggaca catacaaagt tacccacaga ttccgtggat       1800
aagcagggga ctaacatgtg aggcaaaaca gcagggccgc gccggtggcg ttttttcata       1860
ggctccgccc tcctgccaga gttcacataa acagacgctt ttccggtgca tctgtgggag       1920
ccgtgaggct caaccatgaa tctgacagta cgggcgaaac ccgacaggac ttaaagatcc       1980
ccaccgtttc cggcgggtcg ctcccttcttg cgctctcctg ttccgaccct gccgtttacc       2040
ggatacctgt tccgcctttc tcccttacgg gaagtgtggc gctttctcat agctcacaca       2100
ctggtatctc ggctcggtgt aggtcgttcg ctccaagctg ggctgtaagc aagaactccc       2160
cgttcagccc gactgctgcg ccttatccgg taactgttca cttgagtcca acccggaaaa       2220
gcacggtaaa acgccactgg cagcagccat ggtaactgg gagttcgcag aggatttgtt       2280
tagctaaaca cgcggttgct cttgaagtgt gcgccaaagt ccggctacac tggaaggaca       2340
gatttggttg ctgtgctctg cgaaagccag ttaccacggt taagcagttc cccaactgac       2400
ttaaccttcg atcaaaccac ctccccaggt ggttttttcg tttacagggc aaaagattac       2460
gcgcagaaaa aaaggatctc aagaagatcc tttgatcttt tctactgaac cgctctagct       2520
ttcagtgcaa tttatctctt caaatgtagc acctgaagtc agccccatac gatataagtt       2580
gtaattctca tgttagtcat gccccgcgcc caccggaagg agctgactgg gttgaaggct       2640
```

```
ctcaagggca tcggtcgaga tcccggtgcc taatgagtga gctaacttac attaattgcg    2700
ttgcgctcac tgcccgcttt ccagtcggga acctgtcgt gccagctgca ttaatgaatc     2760
ggccaacgcg cggggagagg cggtttgcgt attgggcgcc cgataagctt aattaatctt    2820
tctgcgaatt gagatgacgc cactggctgg gcgtcatccc ggtttccgg gtaaacacca    2880
ccgaaaaata gttactatct tcaaagccac attcggtcga aatatcactg attaacaggc    2940
ggctatgctg gagaagatat tgcgcatgac acactctgac ctgtcgcaga tattgattga    3000
tggtcattcc agtctgctgg cgaaattgct gacgcaaaac gcgctcactg cacgatgcct    3060
catcacaaaa tttatccagc gcaaagggac ttttcaggct agccgccagc cgggtaatca    3120
gcttatccag caacgtttcg ctggatgttg gcggcaacga atcactggtg taacgatggc    3180
gattcagcaa catcaccaac tgcccgaaca gcaactcagc catttcgtta gcaaacggca    3240
catgctgact actttcatgc tcaagctgac cgataacctg ccgcgcctgc gccatcccca    3300
tgctacctaa gcgccagtgt ggttgccctg cgctggcgtt aaatcccgga tcgcccccct    3360
gccagtcaag attcagcttc agacgctccg ggcaataaat aatattctgc aaaaccagat    3420
cgttaacgga agcgtaggag tgtttatcgt cagcatgaat gtaaaagaga tcgccacggg    3480
taatgcgata agggcgatcg ttgagtacat gcaggccatt accgcgccag acaatcacca    3540
gctcacaaaa atcatgtgta tgttcagcaa agacatcttg cggataacgg tcagccacag    3600
cgactgcctg ctggtcgctg gcaaaaaaat catctttgag aagttttaac tgatgcgcca    3660
ccgtggctac ctcggccaga gaacgaagtt gattattcgc aatatggcgt acaaatacgt    3720
tgagaagatt cgcgttattg cagaaagcca tcccgtccct ggcgaatatc acgcggtgac    3780
cagttaaact ctcggcgaaa aagcgtcgaa aagtggttac tgtcgctgaa tccacagcga    3840
taggcgatgt cagtaacgct ggcctcgctg tggcgtagca gatgtcgggc tttcatcagt    3900
cgcaggcggt tcaggtatcg ctgaggcgtc agtcccgttt gctgcttaag ctgccgatgt    3960
agcgtacgca gtgaaagaga aaattgatcc gccacggcat cccaattcac ctcatcggca    4020
aaatggtcct ccagccaggc cagaagcaag ttgagacgtg atgcgctgtt ttccaggttc    4080
tcctgcaaac tgcttttacg cagcaagagc agtaattgca taaacaagat ctcgcgactg    4140
gcggtcgagg gtaaatcatt ttccccttcc tgctgttcca tctgtgcaac cagctgtcgc    4200
acctgctgca atacgctgtg gttaacgcgc cagtgagacg gatactgccc atccagctct    4260
tgtggcagca actgattcag cccggcgaga aactgaaatc gatccggcga gcgatacagc    4320
acattggtca gacacagatt atcggtatgt tcatacagat gccgatcatg atcgcgtacg    4380
aaacagaccg tgccaccggt gatggtatag ggctgcccat taaacacatg aatacccgtg    4440
ccatgttcga caatcacaat ttcatgaaaa tcatgatgat gttcaggaaa atccgcctgc    4500
gggagccggg gttctatcgc cacggacgcg ttaccagacg gaaaaaaatc cacactatgt    4560
aatacggtca tactggcctc ctgatgtcgt caacacggcg aaatagtaat cacgaggtca    4620
ggttcttacc ttaaattttc gacggaaaac cacgtaaaaa acgtcgattt ttcaagatac    4680
agcgtgaatt ttcaggaaat gcggtgagca tcacatcacc acaattcagc aaattgtgaa    4740
catcatcacg ttcatctttc cctggttgcc aatg                               4774
```

<210> SEQ ID NO 3
<211> LENGTH: 4774
<212> TYPE: DNA
<213> ORGANISM: Artificial
<220> FEATURE:
<223> OTHER INFORMATION: pTACO1-LysY plasmid

<400> SEQUENCE: 3

```
gcccattttc ctgtcagtaa cgagaaggtc gcgaattcag gcgcttttta gactggtcgt      60
aatgaaattc aggaggttgt cgacatggct cgtgtacagt ttaaacaacg tgaatctact     120
gacgcaatct ttgttcactg ctcggctacc aagccaagtc agaatgttgg tgtccgtgag     180
attcgccagt ggcacaaaga gcagggttgg ctcgatgtgg ataccactt tatcatcaag      240
cgagacggta ctgtggaggc aggacgagat gagatggctg taggctctca cgctaagggt     300
tacaaccaca actctatcgg cgtctgcctt gttggtggta tcgacgataa aggtaagttc     360
gacgctaact ttacgccagc ccaaatgcaa tcccttcgct cactgcttgt cacactgctg     420
gctaagtacg aaggcgctgt gcttcgcgcc catcatgagg tggcgccgta cgcttgccct     480
tcgttcgacc ttaagcgttg gtgggagaag aacgaactgg tcacttctga ccgtggataa     540
ggatccccgc gccctcatcc gaaagggcgt attcatatgc cctaggctgc tgccaccgct     600
gagcaataac tagcataacc ccttgggggcc tctaaacggg tcttgagggg ttttttgctg    660
aaacctcagg catttgagaa gcacacggtc acactgcttc cggtagtcaa taaaccggta     720
aaccagcaat agacataagc ggctatttaa cgaccctgcc ctgaaccgac gacgggtca      780
tcgtggccgg atcttgcggc ccctcggctt gaacgaattg ttagacatta tttgccgact     840
accttggtga tctcgccttt cacgtagtgg acaaattctt ccaactgatc tgcgcgcgag     900
gccaagcgat cttcttcttg tccaagataa gcctgtctag cttcaagtat gacgggctga     960
tactgggccg gcaggcgctc cattgcccag tcggcagcga catccttcgg cgcgatttttg   1020
ccggttactg cgctgtacca aatgcgggac aacgtaagca ctacatttcg ctcatcgcca    1080
gcccagtcgg gcggcgagtt ccatagcgtt aaggtttcat ttagcgcctc aaatagatcc    1140
tgttcaggaa ccggatcaaa gagttcctcc gccgctggac ctaccaaggc aacgctatgt    1200
tctcttgctt ttgtcagcaa gatagccaga tcaatgtcga tcgtggctgg ctcgaagata    1260
cctgcaagaa tgtcattgcg ctgccattct ccaaattgca gttcgcgctt agctggataa    1320
cgccacggaa tgatgtcgtc gtgcacaaca atggtgactt ctacagcgcg gagaatctcg    1380
ctctctccag gggaagccga agtttccaaa aggtcgttga tcaaagctcg ccgcgttgtt    1440
tcatcaagcc ttacggtcac cgtaaccagc aaatcaatat cactgtgtgg cttcaggccg    1500
ccatccactg cggagccgta caaatgtacg gccagcaacg tcggttcgag atggcgctcg    1560
atgacgccaa ctacctctga tagttgagtc gatacttcgg cgatcaccgc ttccctcata    1620
ctcttccttt ttcaatatta ttgaagcatt tatcagggtt attgtctcat gagcggatac    1680
atatttgaat gtatttagaa aaataaacaa atagctagct cactcggtcg ctacgctccg    1740
ggcgtgagac tgcggcgggc gctgcggaca catacaaagt tacccacaga ttccgtggat    1800
aagcagggga ctaacatgtg aggcaaaaca gcagggccgc gccggtggcg ttttccata     1860
ggctccgccc tcctgccaga gttcacataa acagacgctt ttccggtgca tctgtgggag    1920
ccgtgaggct caaccatgaa tctgacagta cgggcgaaac ccgacaggac ttaaagatcc    1980
ccaccgtttc cggcgggtcg ctccctcttg cgctctcctg ttccgaccct gccgtttacc    2040
ggatacctgt tccgccttc tcccttacgg gaagtgtggc gctttctcat agctcacaca    2100
ctggtatctc ggctcggtgt aggtcgttcg ctccaagctg ggctgtaagc aagaactccc    2160
cgttcagccc gactgctgcg ccttatccgg taactgttca cttgagtcca accggaaaa    2220
gcacggtaaa acgccactgg cagcagccat ggtaactgg gagttcgcag aggatttgtt   2280
tagctaaaca cgcggttgct cttgaagtgt gcgccaaagt ccggctacac tggaaggaca    2340
```

```
gatttggttg ctgtgctctg cgaaagccag ttaccacggt taagcagttc cccaactgac    2400
ttaaccttcg atcaaaccac ctccccaggt ggttttttcg tttacagggc aaaagattac    2460
gcgcagaaaa aaaggatctc aagaagatcc tttgatcttt tctactgaac cgctctagct    2520
ttcagtgcaa tttatctctt caaatgtagc acctgaagtc agccccatac gatataagtt    2580
gtaattctca tgttagtcat gccccgcgcc caccggaagg agctgactgg gttgaaggct    2640
ctcaagggca tcggtcgaga tcccggtgcc taatgagtga gctaacttac attaattgcg    2700
ttgcgctcac tgcccgcttt ccagtcggga aacctgtcgt gccagctgca ttaatgaatc    2760
ggccaacgcg cggggagagg cggtttgcgt attgggcgcc cgataagctt aattaatctt    2820
tctgcgaatt gagatgacgc cactggctgg gcgtcatccc ggtttcccgg gtaaacacca    2880
ccgaaaaata gttactatct tcaaagccac attcggtcga atatcactg attaacaggc    2940 ggctatgctg gagaagatat tgcgcatgac acactctgac ctgtcgcaga tattgattga    3000
tggtcattcc agtctgctgg cgaaattgct gacgcaaaac gcgctcactg cacgatgcct    3060
catcacaaaa tttatccagc gcaaagggac ttttcaggct agccgccagc cgggtaatca    3120
gcttatccag caacgtttcg ctggatgttg gcggcaacga atcactgtg taacgatggc    3180 gattcagcaa catcaccaac tgcccgaaca gcaactcagc catttcgtta gcaaacggca    3240
catgctgact actttcatgc tcaagctgac cgataacctg ccgcgcctgc gccatcccca    3300
tgctacctaa gcgccagtgt ggttgccctg cgctggcgtt aaatcccgga atcgccccct    3360
gccagtcaag attcagcttc agacgctccg ggcaataaat aatattctgc aaaaccagat    3420
cgttaacgga agcgtaggag tgtttatcgt cagcatgaat gtaaaagaga tcgccacggg    3480
taatgcgata agggcgatcg ttgagtacat caggccatt accgcgccag acaatcacca    3540
gctcacaaaa atcatgtgta tgttcagcaa agacatcttg cggataacgg tcagccacag    3600
cgactgcctg ctggtcgctg gcaaaaaaat catctttgag aagttttaac tgatgcgcca    3660
ccgtggctac ctcggccaga gaacgaagtt gattattcgc aatatggcgt acaaatacgt    3720
tgagaagatt cgcgttattg cagaaagcca tcccgtccct ggcgaatatc acgcggtgac    3780
cagttaaact ctcggcgaaa aagcgtcgaa aagtggttac tgtcgctgaa tccacagcga    3840
taggcgatgt cagtaacgct ggcctcgctg tggcgtagca gatgtcgggc tttcatcagt    3900
cgcaggcggt tcaggtatcg ctgaggcgtc agtcccgttt gctgcttaag ctgccgatgt    3960
agcgtacgca gtgaaagaga aaattgatcc gccacggcat cccaattcac ctcatcggca    4020
aaatggtcct ccagccaggc cagaagcaag ttgagacgtg atgcgctgtt ttccaggttc    4080
tcctgcaaac tgcttttacg cagcaagagc agtaattgca taaacaagat ctcgcgactg    4140
gcggtcgagg gtaaatcatt ttccccttcc tgctgttcca tctgtgcaac cagctgtcgc    4200
acctgctgca atacgctgtg gttaacgcgc cagtgagacg gatactgccc atccagctct    4260
tgtggcagca actgattcag cccggcgaga aactgaaatc gatccggcga gcgatacagc    4320
acattggtca gacacagatt atcggtatgt tcatacagat gccgatcatg atcgcgtacg    4380
aaacagaccg tgccaccggt gatggtatag ggctgcccat taaacacatg aatacccgtg    4440
ccatgttcga caatcacaat ttcatgaaaa tcatgatgat gttcaggaaa atccgcctgc    4500
gggagccggg gttctatcgc cacggacgcg ttaccagacg gaaaaaaatc cacactatgt    4560
aatacggtca tactggcctc ctgatgtcgt caacacggcg aaatagtaat cacgaggtca    4620
ggttcttacc ttaaattttc gacggaaaac cacgtaaaaa acgtcgattt ttcaagatac    4680
agcgtgaatt ttcaggaaat gcggtgagca tcacatcacc acaattcagc aaattgtgaa    4740
```

| | |
|---|---:|
| catcatcacg ttcatctttc cctggttgcc aatg | 4774 |

<210> SEQ ID NO 4
<211> LENGTH: 5001
<212> TYPE: DNA
<213> ORGANISM: Artificial
<220> FEATURE:
<223> OTHER INFORMATION: pTACO2-Lys plasmid

<400> SEQUENCE: 4

| | |
|---|---:|
| gcccattttc ctgtcagtaa cgagaaggtc gcgaattcag gcgctttta gactggtcgt | 60 |
| aatgaaattc aggaggtggt cgacatggct cgtgtacagt ttaaacaacg tgaatctact | 120 |
| gacgcaatct tgttcactg ctcggctacc aagccaagtc agaatgttgg tgtccgtgag | 180 |
| attcgccagt ggcacaaaga gcaggggttgg ctcgatgtgg ataccactt tatcatcaag | 240 |
| cgagacggta ctgtggaggc aggacgagat gagatggctg taggctctca cgctaagggt | 300 |
| tacaaccaca actctatcgg cgtctgcctt gttggtggta tcgacgataa aggtaagttc | 360 |
| gacgctaact ttacgccagc ccaaatgcaa tcccttcgct cactgcttgt cacactgctg | 420 |
| gctaagtacg aaggcgctgt gcttcgcgcc catcatgagg tggcgccgaa agcttgccct | 480 |
| tcgttcgacc ttaagcgttg gtgggagaag aacgaactgg tcacttctga ccgtggataa | 540 |
| ggatccccgc gccctcatcc gaaagggcgt attcatatgc cctaggctgc tgccaccgct | 600 |
| gagcaataac tagcataacc ccttggggcc tctaaacggg tcttgagggg ttttttgctg | 660 |
| aaacctcagg catttgagaa gcacacggtc acactgcttc cggtagtcaa taaaccggta | 720 |
| aaccagcaat agacataagc ggctatttaa cgaccctgcc ctgaaccgac gaccgggtcg | 780 |
| aatttgcttt cgaatttctg ccattcatcc gcttattatc acttattcag gcgtagcacc | 840 |
| aggcgtttaa gggcaccaat aactgcctta aaaaaattac gccccgccct gccactcatc | 900 |
| gcagtactgt tgtaattcat taagcattct gccgacatgg aagccatcac aaacggcatg | 960 |
| atgaacctga atcgccagcg gcatcagcac cttgtcgcct tgcgtataat atttgcccat | 1020 |
| agtgaaaacg ggggcgaaga gttgtccat attggccacg tttaaatcaa actggtgaa | 1080 |
| actcacccag ggattggctg agacgaaaaa catattctca ataaaccctt tagggaaata | 1140 |
| ggccaggttt tcaccgtaac acgccacatc ttgcgaatat atgtgtagaa actgccggaa | 1200 |
| atcgtcgtgg tattcactcc agagcgatga aaacgttca gtttgctcat ggaaaacggt | 1260 |
| gtaacaaggg tgaacactat cccatatcac cagctcaccg tctttcattg ccatacggaa | 1320 |
| ctccggatga gcattcatca ggcgggcaag aatgtgaata aaggccggat aaaacttgtg | 1380 |
| cttattttc tttacggtct ttaaaaaggc cgtaatatcc agctgaacgg tctggttata | 1440 |
| ggtacattga gcaactgact gaaatgcctc aaaatgttct ttacgatgcc attgggatat | 1500 |
| atcaacggtg gtatatccag tgatttttt ctccatttta gcttccttag ctcctgaaaa | 1560 |
| tctcgataac tcaaaaaata cgcccggtag tgatcttatt tcattatggt gaaagttgga | 1620 |
| acctcttacg tgccgatcaa cgtctcattt tcgccaaaag ttgggccagg cttcccggt | 1680 |
| atcaacaggg acaccaggat ttatttattc tgcgaagtga tcttccgtca caggtattta | 1740 |
| ttcggcgcaa agtgcgtcgg gtgatgctgc caacttactg atttagtgta tgatggtgtt | 1800 |
| tttgaggtgc tccagtggct tctgttctcta tcagctgtcc ctcctgttca gctactgacg | 1860 |
| gggtggtgcg taacggcaaa agcaccgccg gacatcagcg ctagcggagt gtatactggc | 1920 |
| ttactatgtt ggcactgatg agggtgtcag tgaagtgctt catgtggcag agaaaaaaag | 1980 |
| gctgcaccgg tgcgtcagca gaatatgtga tacaggatat attccgcttc ctcgctcact | 2040 |

```
gactcgctac gctcggtcgt tcgactgcgg cgagcggaaa tggcttacga acggggcgga   2100
gatttcctgg aagatgccag gaagatactt aacaggaag tgagagggcc gcggcaaagc    2160
cgttttccca taggctccgc cccctgaca agcatcacga aatctgacgc tcaaatcagt    2220
ggtggcgaaa cccgacagga ctataaagat accaggcgtt tccctggcg gctccctcgt    2280 gcgctctcct gttcctgcct ttcggtttac cggtgtcatt ccgctgttat ggccgcgttt   2340
gtctcattcc acgcctgaca ctcagttccg ggtaggcagt tcgctccaag ctggactgta   2400
tgcacgaacc ccccgttcag tccgaccgct gcgccttatc cggtaactat cgtcttgagt   2460
ccaacccgga aagacatgca aaagcaccac tggcagcagc cactggtaat tgatttagag   2520
gagttagtct tgaagtcatg cgccggttaa ggctaaactg aaaggacaag ttttggtgac   2580
tgcgctcctc caagccagtt acctcggttc aaagagttgg tagctcagag aaccttcgaa   2640
aaaccgccct gcaaggcggt tttttcgttt tcagagcaag agattacgcg cagaccaaaa   2700
cgatctcaag aagatcatct tattaatcag ataaaatatt tctaggtttc agtgcaattt   2760
atctcttcaa atgtagcacc tgaagtcagc cccatacgat ataagttgta attctcatgt   2820
tagtcatgcc ccgcgcccac cggaaggagc tgactgggtt gaaggctctc aagggcatcg   2880
gtcgagatcc cggtgcctaa tgagtgagct aacttacatt aattgcgttg cgctcactgc   2940
ccgcttccca gtcgggaaac ctgtcgtgcc agctgcatta atgaatcggc caacgcgcgg   3000
ggagaggcgg tttgcgtatt gggcgcccga taagcttaat taatctttct gcgaattgag   3060
atgacgccac tggctgggcg tcatcccggt ttcccgggta acaccaccg aaaaatagtt    3120 actatcttca aagccacatt cggtcgaaat atcactgatt aacaggcggc tatgctggag   3180
aagatattgc gcatgacaca ctctgacctg tcgcagatat tgattgatgg tcattccagt   3240
ctgctggcga aattgctgac gcaaaacgcg ctcactgcac gatgcctcat cacaaaattt   3300
atccagcgca aagggacttt tcaggctagc cgccagccgg gtaatcagct tatccagcaa   3360
cgtttcgctg gatgttggcg gcaacgaatc actggtgtaa cgatggcgat tcagcaacat   3420
caccaactgc ccgaacagca actcagccat ttcgttagca aacggacat gctgactact   3480 ttcatgctca agctgaccga taacctgccg cgcctgcgcc atccccatgc tacctaagcg   3540
ccagtgtggt tgccctgcgc tggcgttaaa tcccggaatc gccccctgcc agtcaagatt   3600
cagcttcaga cgctccgggc aataaataat attctgcaaa accagatcgt taacggaagc   3660
gtaggagtgt ttatcgtcag catgaatgta aaagagatcg ccacgggtaa tgcgataagg   3720
gcgatcgttg agtacatgca ggccattacc gcgccagaca atcaccagct cacaaaaatc   3780
atgtgtatgt tcagcaaaga catcttgcgg ataacggtca gccacagcga ctgcctgctg   3840
gtcgctggca aaaaaatcat cttttgagaag ttttaactga tgcgccaccg tggctacctc   3900
ggccagagaa cgaagttgat tattcgcaat atggcgtaca aatacgttga agattcgc     3960 gttattgcag aaagccatcc cgtccctggc gaatatcacg cggtgaccag ttaaactctc   4020
ggcgaaaaag cgtcgaaaag tggttactgt cgctgaatcc acagcgatag gcgatgtcag   4080
taacgctggc ctcgctgtgg cgtagcagat gtcgggcttt catcagtcgc aggcggttca   4140
ggtatcgctg aggcgtcagt cccgtttgct gcttaagctg ccgatgtagc gtacgcagtg   4200
aaagagaaaa ttgatccgcc acggcatccc aattcacctc atcggcaaaa tggtcctcca   4260
gccaggccag aagcaagttg agacgtgatg cgctgttttc caggttctcc tgcaaactgc   4320
ttttacgcag caagagcagt aattgcataa acaagatctc gcgactggcg gtcgaggta    4380 aatcattttc cccttcctgc tgttccatct gtgcaaccag ctgtcgcacc tgctgcaata   4440
```

```
cgctgtggtt aacgcgccag tgagacggat actgcccatc cagctcttgt ggcagcaact    4500
gattcagccc ggcgagaaac tgaaatcgat ccggcgagcg atacagcaca ttggtcagac    4560
acagattatc ggtatgttca tacagatgcc gatcatgatc gcgtacgaaa cagaccgtgc    4620
caccggtgat ggtatagggc tgcccattaa acacatgaat acccgtgcca tgttcgacaa    4680
tcacaatttc atgaaaatca tgatgatgtt caggaaaatc cgcctgcggg agccggggtt    4740
ctatcgccac ggacgcgtta ccagacgaa aaaaatccac actatgtaat acggtcatac     4800
tggcctcctg atgtcgtcaa cacggcgaaa tagtaatcac gaggtcaggt tcttacctta    4860
aattttcgac ggaaaaccac gtaaaaaacg tcgatttttc aagatacagc gtgaattttc    4920
aggaaatgcg gtgagcatca catcaccaca attcagcaaa ttgtgaacat catcacgttc    4980
atctttccct ggttgccaat g                                              5001

<210> SEQ ID NO 5
<211> LENGTH: 6358
<212> TYPE: DNA
<213> ORGANISM: Artificial
<220> FEATURE:
<223> OTHER INFORMATION: pTACO3-LysY plasmid

<400> SEQUENCE: 5
gcccattttc ctgtcagtaa cgagaaggtc gcgaattcag gcgcttttta gactggtcgt      60
aatgaaattc aggaggttgt cgacatggct cgtgtacagt ttaaacaacg tgaatctact     120
gacgcaatct tgttcactg ctcggctacc aagccaagtc agaatgttgg tgtccgtgag      180
attcgccagt ggcacaaaga gcagggttgg ctcgatgtgg ataccacctt tatcatcaag     240
cgagacggta ctgtggaggc aggacgagat gagatggctg taggctctca cgctaagggt     300
tacaaccaca actctatcgg cgtctgcctt gttggtggta tcgacgataa aggtaagttc     360
gacgctaact ttacgccagc ccaaatgcaa tcccttcgct cactgcttgt cacactgctg     420
gctaagtacg aaggcgctgt gcttcgcgcc catcatgagg tggcgccgta cgcttgccct     480
tcgttcgacc ttaagcgttg gtgggagaag aacgaactgg tcacttctga ccgtggataa     540
ggatccccgc gccctcatcc gaaagggcgt attcatatgc cctagggaca gtaagacggg     600
taagcctgtt gatgataccg ctgccttact gggtgcatta gccagtctga atgacctgtc     660
acgggataat ccgaagtggt cagactgaa atcagagggg caggaactgc tgaacagcaa      720
aaagtcagat agcaccacat agcagacccg ccataaaacg ccctgagaag cccgtgacgg     780
gctttttctg tattatgggt agtttccttg catgaatcca taaaaggcgc ctgtagtgcc     840 attaccccc attcactgcc agagccgtga gcgcagcgaa ctgaatgtca gaaaaagac       900 agcgactcag gtgcctgatg gtcggagaca aaggaatat tcagcgattt gcccgagctt      960
gcgagggtgc tacttaagcc tttagggttt taaggtctgt tttgtagagg agcaaacagc    1020
gtttgcgaca tccttttgta atactgcgga actgactaaa gtagtgagtt atacacaggg    1080
ctgggatcta ttcttttat cttttttat tctttcttta ttctataaat tataaccact      1140
tgaatataaa caaaaaaac acacaaaggt ctagcgaat ttacgagggg tctagcagaa      1200
tttacaagtt ttccagcaaa ggtctagcag aatttacaga tacccacaac tcaaaggaaa    1260
aggactagta attatcattg actagcccat ctcaattggt atagtgatta aaatcaccta    1320
gaccaattga gatgtatgtc tgaattagtt gttttcaaag caaatgaact agcgattagt    1380
cgctatgact taacggagca tgaaccaag ctaattttat gctgtgtggc actactcaac      1440
cccacgattg aaaaccctac aaggaaagaa cggacggtat cgttcactta taaccaatac    1500
```

```
gctcagatga tgaacatcag tagggaaaat gcttatggtg tattagctaa agcaaccaga      1560
gagctgatga cgagaactgt ggaaatcagg aatcctttgg ttaaaggctt tgagattttc      1620
cagtggacaa actatgccaa gttctcaagc gaaaaattag aattagtttt tagtgaagag      1680
atattgcctt atcttttcca gttaaaaaaa ttcataaaat ataatctgga acatgttaag      1740
tcttttgaaa acaaatactc tatgaggatt tatgagtggt tattaaaaga actaacacaa      1800
aagaaaactc acaaggcaaa tatagagatt agccttgatg aatttaagtt catgttaatg      1860
cttgaaaata actaccatga gtttaaaagg cttaaccaat gggttttgaa accaataagt      1920
aaagatttaa acacttacag caatatgaaa ttggtggttg ataagcgagg ccgcccgact      1980
gatacgttga ttttccaagt tgaactagat agacaaatgg atctcgtaac cgaacttgag      2040
aacaaccaga taaaaatgaa tggtgacaaa ataccaacaa ccattacatc agattcctac      2100
ctacataacg gactaagaaa aacactacac gatgctttaa ctgcaaaaat tcagctcacc      2160
agttttgagg caaattttt gagtgacatg caaagtaagt atgatctcaa tggttcgttc      2220
tcatggctca cgcaaaaaca acgaaccaca ctagagaaca tactggctaa atacggaagg      2280
atctgaggtt cttatggctc ttgtatctat cagtgaagca tcaagactaa caaacaaaag      2340
tagaacaact gttcaccgtt acatatcaaa gggaaaactg tccatatgca cagatgaaaa      2400
cggtgtaaaa aagatagata catcagagct tttacgagtt tttggtgcat tcaaagctgt      2460
tcaccatgaa cagatcgaca atgtaacaga tgaacagcat gtaacaccta atagaacagg      2520
tgaaaccagt aaaacaaagc aactagaaca tgaaattgaa cacctgagac aacttgttac      2580
agctcaacag tcacacatag acagcctgaa acaggcgatg ctgcttatcg aatcaaagct      2640
gccgacaaca cggagccag tgacgcctcc cgtggggaaa aaatcatggc aattctggaa      2700
gaaatagcgc tttcagccgg caaaccggct gaagccggat ctgcgattct gataacaaac      2760
tagcaacacc agaacagccc gtttgcgggc agcaaaaccc gtgggaatta attcccctgc      2820
tcgcgcaggc tgggtgccaa gctctcgggt aacatcaagg cccgatcctt ggagcccttg      2880
ccctcccgca cgatgatcgt gccgtgatcg aaatccagat ccttgacccg cagttgcaaa      2940
ccctcactga tccgcatgcc cgttccatac agaagctggg cgaacaaacg atgctcgcct      3000
tccagaaaac cgaggatgcg aaccacttca tccggggtca gcaccaccgg caagcgccgc      3060
gacggccgag gtcttccgat ctcctgaagc cagggcagat ccgtgcacag cacccttgccg     3120 tagaagaaca gcaaggccgc caatgcctga cgatgcgtgg agaccgaaac cttgcgctcg      3180
ttcgccagcc aggacagaaa tgcctcgact tcgctgctgc ccaaggttgc cgggtgacgc      3240
acaccgtgga aacggatgaa ggcacgaacc cagtggacat aagcctgttc ggttcgtaag      3300
ctgtaatgca agtagcgtat gcgctcacgc aactggtcca gaaccttgac cgaacgcagc      3360
ggtggtaacg gcgcagtggc ggttttcatg gcttgttatg actgttttt tggggtacag      3420 tctatgcctc gggcatccaa gcagcaagcg cgttacgccg tgggtcgatg tttgatgtta      3480
tggagcagca acgatgttac gcagcagggc agtcgcccta aaacaaagtt aaacatcatg      3540
agggaagcgg tgatcgccga agtatcgact caactatcag aggtagttgg cgtcatcgag      3600
cgccatctcg aaccgacgtt gctggccgta catttgtacg gctccgcagt ggatggcggc      3660
ctgaagccac acagtgatat tgatttgctg gttacggtga ccgtaaggct tgatgaaaca      3720
acgcggcgag ctttgatcaa cgaccttttg gaaacttcgg cttcccctgg agagagcgag      3780
attctccgcg ctgtagaagt caccattgtt gtgcacgacg acatcattcc gtggcgttat      3840
ccagctaagc gcgaactgca atttggagaa tggcagcgca atgacattct tgcaggtatc      3900
```

```
ttcgagccag ccacgatcga cattgatctg gctatcttgc tgacaaaagc aagagaacat    3960
agcgttgcct tggtaggtcc agcggcggag gaactctttg atccggttcc tgaacaggat    4020
ctatttgagg cgctaaatga aaccttaacg ctatggaact cgccgcccga ctgggctggc    4080
gatgagcgaa atgtagtgct tacgttgtcc cgcatttggt acagcgcagt aaccggcaaa    4140
atcgcgccga aggatgtcgc tgccgactgg gcaatggagc gcctgccggc ccagtatcag    4200
cccgtcatac ttgaagctag acaggcttat cttggacaag aagaagatcg cttggcctcg    4260
cgcgcagatc agttggaaga atttgtccac tacgtgaaag gcgagatcac caaggtagtc    4320
ggcaaataat gtctaacaat tcgttcaagc cgacgccgct tcgcggcgcg gcttaactca    4380
agcgttagaa gcttaattaa tctttctgcg aattgagatg acgccactgg ctgggcgtca    4440
tcccggtttc ccgggtaaac accaccgaaa aatagttact atcttcaaag ccacattcgg    4500
tcgaaatatc actgattaac aggcggctat gctggagaag atattgcgca tgacacactc    4560
tgacctgtcg cagatattga ttgatggtca ttccagtctg ctggcgaaat tgctgacgca    4620
aaacgcgctc actgcacgat gcctcatcac aaaatttatc cagcgcaaag ggacttttca    4680
ggctagccgc cagccgggta atcagcttat ccagcaacgt ttcgctggat gttggcggca    4740
acgaatcact ggtgtaacga tggcgattca gcaacatcac caactgcccg aacagcaact    4800
cagccatttc gttagcaaac ggcacatgct gactactttc atgctcaagc tgaccgataa    4860
cctgccgcgc ctgcgccatc cccatgctac ctaagcgcca gtgtggttgc cctgcgctgg    4920
cgttaaatcc cggaatcgcc ccctgccagt caagattcag cttcagacgc tccgggcaat    4980
aaataatatt ctgcaaaacc agatcgttaa cggaagcgta ggagtgttta tcgtcagcat    5040
gaatgtaaaa gagatcgcca cgggtaatgc gataagggcg atcgttgagt acatgcaggc    5100
cattaccgcg ccagacaatc accagctcac aaaaatcatg tgtatgttca gcaaagacat    5160
cttgcggata acgtcagcc acagcgactg cctgctggtc gctggcaaaa aaatcatctt    5220
tgagaagttt taactgatgc gccaccgtgg ctacctcggc cagagaacga agttgattat    5280
tcgcaatatg gcgtacaaat acgttgagaa gattcgcgtt attgcagaaa gccatcccgt    5340
ccctggcgaa tatcacgcgg tgaccagtta aactctcggc gaaaaagcgt cgaaaagtgg    5400
ttactgtcgc tgaatccaca gcgataggcg atgtcagtaa cgctggcctc gctgtggcgt    5460
agcagatgtc gggctttcat cagtcgcagg cggttcaggt atcgctgagg cgtcagtccc    5520
gtttgctgct taagctgccg atgtagcgta cgcagtgaaa gagaaaattg atccgccacg    5580
gcatcccaat tcacctcatc ggcaaaatgg tcctccagcc aggccagaag caagttgaga    5640
cgtgatgcgc tgttttccag gttctcctgc aaactgcttt tacgcagcaa gagcagtaat    5700
tgcataaaca agatctcgcg actggcggtc gagggtaaat catttccccc ttcctgctgt    5760
tccatctgtg caaccagctg tcgcacctgc tgcaatacgc tgtggttaac gcgccagtga    5820
gacggatact gcccatccag ctcttgtggc agcaactgat tcagcccggc gagaaactga    5880
aatcgatccg gcgagcgata cagcacattg gtcagacaca gattatcggt atgttcatac    5940
agatgccgat catgatcgcg tacgaaacag accgtgccac cggtgatggt atagggctgc    6000
ccattaaaca catgaatacc cgtgccatgt tcgacaatca caatttcatg aaaatcatga    6060
tgatgttcag gaaaatccgc ctgcgggagc cggggttcta tcgccacgga cgcgttacca    6120
gacggaaaaa aatccacact atgtaatacg gtcatactgg cctcctgatg tcgtcaacac    6180
ggcgaaaatag taatcacgag gtcaggttct taccttaaat tttcgacgga aaaccacgta    6240
aaaaacgtcg atttttcaag atacagcgtg aattttcagg aaatgcggtg agcatcacat    6300
```

```
caccacaatt cagcaaattg tgaacatcat cacgttcatc tttccctggt tgccaatg          6358
```

<210> SEQ ID NO 6
<211> LENGTH: 72
<212> TYPE: DNA
<213> ORGANISM: Artificial
<220> FEATURE:
<223> OTHER INFORMATION: rhaBAD promoter

<400> SEQUENCE: 6

```
gcccattttc ctgtcagtaa cgagaaggtc gcgaattcag gcgcttttta gactggtcgt      60
aatgaaattc ag                                                          72
```

<210> SEQ ID NO 7
<211> LENGTH: 38
<212> TYPE: DNA
<213> ORGANISM: Artificial
<220> FEATURE:
<223> OTHER INFORMATION: pRha_EheI_f

<400> SEQUENCE: 7

```
gcgcgcggcg cccgataagc ttaattaatc tttctgcg                              38
```

<210> SEQ ID NO 8
<211> LENGTH: 37
<212> TYPE: DNA
<213> ORGANISM: Artificial
<220> FEATURE:
<223> OTHER INFORMATION: pRha_XmaJI_r

<400> SEQUENCE: 8

```
cgcgcgccta gggcatatga atacgcccct tcggatg                               37
```

<210> SEQ ID NO 9
<211> LENGTH: 32
<212> TYPE: DNA
<213> ORGANISM: Artificial
<220> FEATURE:
<223> OTHER INFORMATION: T7Lys_SalI_f

<400> SEQUENCE: 9

```
gcgcgcgtcg acatggctcg tgtacagttt aa                                    32
```

<210> SEQ ID NO 10
<211> LENGTH: 32
<212> TYPE: DNA
<213> ORGANISM: Artificial
<220> FEATURE:
<223> OTHER INFORMATION: T7Lys_BamHI_r

<400> SEQUENCE: 10

```
cgcgcgggat ccttatccac ggtcagaagt ga                                    32
```

<210> SEQ ID NO 11
<211> LENGTH: 32
<212> TYPE: DNA
<213> ORGANISM: Artificial
<220> FEATURE:
<223> OTHER INFORMATION: pCL1920_XmaJI_f

<400> SEQUENCE: 11

```
cgcgcgccta gggacagtaa gacgggtaag cc                                    32
```

<210> SEQ ID NO 12
<211> LENGTH: 32
<212> TYPE: DNA

```
<213> ORGANISM: Artificial
<220> FEATURE:
<223> OTHER INFORMATION: pCL1920_HindIII_r

<400> SEQUENCE: 12
gcgcgcaagc ttctaacgct tgagttaagc cg                                    32

<210> SEQ ID NO 13
<211> LENGTH: 36
<212> TYPE: DNA
<213> ORGANISM: Artificial
<220> FEATURE:
<223> OTHER INFORMATION: Tet promoter

<400> SEQUENCE: 13
ttgacactct atcattgata gagttatttt accact                                36

<210> SEQ ID NO 14
<211> LENGTH: 81
<212> TYPE: DNA
<213> ORGANISM: Artificial
<220> FEATURE:
<223> OTHER INFORMATION: araBAD promoter

<400> SEQUENCE: 14
ccataagatt agcggatcct acctgacgct ttttatcgca actctctact gtttctccat      60
acccgttttt ttggatggag t                                                81

<210> SEQ ID NO 15
<211> LENGTH: 81
<212> TYPE: DNA
<213> ORGANISM: Artificial
<220> FEATURE:
<223> OTHER INFORMATION: rhaBAD

<400> SEQUENCE: 15
gcccattttc ctgtcagtaa cgagaaggtc gcgaattcag gcgcttttta gactggtcgt      60
aatgaaattc agcaggatca c                                                81

<210> SEQ ID NO 16
<211> LENGTH: 456
<212> TYPE: DNA
<213> ORGANISM: Bacteriophage T7

<400> SEQUENCE: 16
atggctcgtg tacagtttaa acaacgtgaa tctactgacg caatctttgt tcactgctcg      60
gctaccaagc caagtcagaa tgttggtgtc cgtgagattc gccagtggca caaagagcag     120
ggttggctcg atgtgggata ccactttatc atcaagcgag acggtactgt ggaggcagga     180
cgagatgaga tggctgtagg ctctcacgct aagggttaca accacaactc tatcggcgtc     240
tgccttgttg gtgtatcga cgataaaggt aagttcgacg ctaactttac gccagcccaa     300
atgcaatccc ttcgctcact gcttgtcaca ctgctggcta agtacgaagg cgctgtgctt     360
cgcgcccatc atgaggtggc gccgaaagct tgcccttcgt tcgaccttaa gcgttggtgg     420
gagaagaacg aactggtcac ttctgaccgt ggataa                               456

<210> SEQ ID NO 17
<211> LENGTH: 2820
<212> TYPE: DNA
<213> ORGANISM: Bacteriophage T7

<400> SEQUENCE: 17
```

-continued

```
tcgcgctgca ctggcgtaat gctgaccgga tggctatcgc taatggtctt acgctcaaca    60
ttgataagca acttgacgca atgttaatgg gctgatagtc ttatcttaca ggtcatctgc   120
gggtggcctg aataggtacg atttactaac tggaagaggc actaaatgaa cacgattaac   180
atcgctaaga acgacttctc tgacatcgaa ctggctgcta tcccgttcaa cactctggct   240
gaccattacg gtgagcgttt agctcgcgaa cagttggccc ttgagcatga gtcttacgag   300
atgggtgaag cacgcttccg caagatgttt gagcgtcaac ttaaagctgg tgaggttgcg   360
gataacgctg ccgccaagcc tctcatcact accctactcc ctaagatgat gcacgcatc    420
aacgactggt ttgaggaagt gaaagctaag cgcggcaagc gcccgacagc cttccagttc   480
ctgcaagaaa tcaagccgga agccgtagcg tacatcacca ttaagaccac tctggcttgc   540
ctaaccagtg ctgacaatac aaccgttcag gctgtagcaa cgcaatcgg tcgggccatt    600
gaggacgagg ctcgcttcgg tcgtatccgt gaccttgaag ctaagcactt caagaaaaac   660
gttgaggaac aactcaacaa gcgcgtaggg cacgtctaca agaaagcatt tatgcaagtt   720
gtcgaggctg acatgctctc taagggtcta ctcggtggcg aggcgtggtc ttcgtggcat   780
aaggaagact ctattcatgt aggagtacgc tgcatcgaga tgctcattga gtcaaccgga   840
atggttagct tacaccgcca aaatgctggc gtagtaggtc aagactctga gactatcgaa   900
ctcgcacctg aatacgctga ggctatcgca acccgtgcag gtgcgctggc tggcatctct   960
ccgatgttcc aaccttgcgt agttcctcct aagccgtgga ctggcattac tggtggtggc  1020
tattgggcta acggtcgtcg tcctctggcg ctggtgcgta ctcacagtaa gaaagcactg  1080
atgcgctacg aagacgttta catgcctgag gtgtacaaag cgattaacat tgcgcaaaac  1140
accgcatgga aaatcaacaa gaaagtccta gcggtcgcca acgtaatcac caagtggaag  1200
cattgtccgg tcgaggacat ccctgcgatt gagcgtgaag aactcccgat gaaaccggaa  1260
gacatcgaca tgaatcctga ggctctcacc gcgtggaaac gtgctgccgc tgctgtgtac  1320
cgcaaggaca gggctcgcaa gtctcgccgt atcagccttg agttcatgct tgagcaagcc  1380
aataagtttg ctaaccataa ggccatctgg ttcccttaca acatggactg gcgcggtcgt  1440
gtttacgccg tgtcaatgtt caacccgcaa ggtaacgata tgaccaaagg actgcttacg  1500
ctggcgaaag gtaaaccaat cggtaaggaa ggttactact ggctgaaaat ccacggtgca  1560
aactgtgcgg tgtcgataa ggttccgttc cctgagcgca tcaagttcat tgaggaaaac  1620
cacgagaaca tcatggcttg cgctaagtct ccactggaga acacttggtg ggctgagcaa  1680
gattctccgt tctgcttcct tgcgttctgc tttgagtacg ctggggtaca gcaccacggc  1740
ctgagctata actgctccct tccgctggcg tttgacgggt cttgctctgg catccagcac  1800
ttctccgcga tgctccgaga tgaggtaggt ggtcgcgcgg ttaacttgct tcctagtgag  1860
accgttcagg acatctacgg gattgttgct aagaaagtca acgagattct acaagcagac  1920
gcaatcaatg gaccgataa cgaagtagtt accgtgaccg atgagaacac tggtgaaatc  1980
tctgagaaag tcaagctggg cactaaggca ctggctggtc aatggctggc tcacggtgtt  2040
actcgcagtg tgactaagcg ttcagtcatg acgctggctt acgggtccaa agagttcggc  2100
ttccgtcaac aagtgctgga agataccatt cagccagcta ttgattccgg caagggtccg  2160
atgttcactc agccgaatca ggctgctgga tacatggcta agctgatttg gaatctgtg   2220
agcgtgacgg tggtagctgc ggttgaagca atgaactggc ttaagtctgc tgctaagctg  2280
ctggctgctg aggtcaaaga taagaagact ggagagattc ttcgcaagcg ttgcgctgtg  2340
cattgggtaa ctcctgatgg tttccctgtg tggcaggaat acaagaagcc tattcagacg  2400
```

```
cgcttgaacc tgatgttcct cggtcagttc cgcttacagc ctaccattaa caccaacaaa    2460
gatagcgaga ttgatgcaca caaacaggag tctggtatcg ctcctaactt tgtacacagc    2520
caagacggta gccaccttcg taagactgta gtgtgggcac acgagaagta cggaatcgaa    2580
tcttttgcac tgattcacga ctccttcggt accattccgg ctgacgctgc gaacctgttc    2640
aaagcagtgc gcgaaactat ggttgacaca tatgagtctt gtgatgtact ggctgatttc    2700
tacgaccagt tcgctgacca gttgcacgag tctcaattgg acaaaatgcc agcacttccg    2760
gctaaaggta acttgaacct ccgtgacatc ttagagtcgg acttcgcgtt cgcgtaacgc    2820
```